United States Patent [19]

Jacobson et al.

[11] Patent Number: 5,324,832

[45] Date of Patent: Jun. 28, 1994

[54] MUSCARINIC ANTAGONISTS

[75] Inventors: Kenneth A. Jacobson, Silver Spring, Md.; Barton J. Bradbury, West Chester, Ohio; Yishai Karton, Nes Ziona, Israel

[73] Assignee: The United States of America as represented by the Department of Health and Human Services, Washington, D.C.

[21] Appl. No.: 725,066

[22] Filed: Jul. 3, 1991

[51] Int. Cl.⁵ .................. C07D 487/04; C07D 513/14; A61K 31/55; A61K 39/395
[52] U.S. Cl. .................. 540/495; 530/391.1; 530/391.5; 424/7.1
[58] Field of Search .......................................... 540/495

[56] References Cited

U.S. PATENT DOCUMENTS

| | | | |
|---|---|---|---|
| 3,660,380 | 5/1972 | Schmidt et al. | 540/495 |
| 4,213,984 | 7/1980 | Schmidt et al. | 540/495 |
| 4,213,985 | 7/1980 | Schmidt et al. | 540/495 |
| 4,381,301 | 4/1983 | Rainer | 540/495 |

*Primary Examiner*—Robert T. Bond
*Attorney, Agent, or Firm*—Leydig, Voit & Mayer

[57] ABSTRACT

Muscarinic antagonists formed by substitution of the distal N-methyl group of pirenzepine or telenzepine. The group used for substitution can be, for example, a propargyl group, a benzyl group, a substituted benzyl group, a hydroxyethyl group, a chloroethyl group, an aminoethyl group, an ω-amino alkyl group, or an N-substituted ω-amino alkyl group.

10 Claims, 8 Drawing Sheets

42a fluorescein conjugate not shown:
42b tetramethylrhodamine conjugate
  c NBD conjugate
  d Texas red conjugate

MUSCARINIC ANTAGONISTS

This invention relates to muscarinic antagonists which are derivatives of pirenzepine and telenzepine. Specifically, these derivatives are formed by alkyl substitution of the distal N-methyl group of pirenzepine or telenzepine. This results in a structurally versatile class of muscarinic antagonists which are useful not only as high affinity receptor probes, but have potential clinical uses, such as for the prevention of gastric acid production in humans.

BACKGROUND OF THE INVENTION

Muscarinic cholinergic receptors (mAChRs) mediate the actions of the neurotransmitter acetylcholine in the central and peripheral nervous systems, gastrointestinal system, heart, endocrine glands, lungs, and other tissues. See *Central Cholinergic Synaptic Transmission*, M. Frotscher and U. Misgeld, eds., Birkhauser Verlag, Basel, 1989; Kromer, W.; Gönne, S.; *Int. J. Exp. Clin. Pharmacol.*, 1988, 37 (suppl. 1), 48; Melchiorre, C.; Cassinelli, A.; Quaglia, W.; *J. Med. Chem.*, 1987, 30, 201; Melchiorre, C.; Cassinelli, A.; Angeli, P.; Giardina, D.; Gulini, U.; Quaglia, W.; *Trends Pharm. Sci. supplement* 1988, 55; Goyal, R.; *New England J. Med.*, 1989, 321, 1022; and Maclagan, J.; Barnes, P., *Trends Pharamcol. Sci* 1989 (Suppl. "Subtypes of Muscarinic Receptors IV"), ed. R. Levine and N.J.M. Birdsall, pp. 88–92, which are specifically incorporated by reference herein.

At least five distinct gene products have been identified which code for five distinct mAChRs, termed m1 through m5. See Bonner, T.I; Buckley, N.J.; Young, A.C.; Brann, M.R.; *Science* 1987, 237, 527; Bonner, T.I; Young, A.C.; Brann, M.R.; Buckley, N.J.; *Neuron* 1988, 1, 403; Peralta, E.G.; Ashkenazi, A.; Winslow, J.W.; Ramachandran, J.; Capon, D.J.; *Nature* 1988, 334, 434; and Maeda, A.; Kubo, T.; Mishina, M.; Numa, S., *FEBS Lett.* 1988, 239, 339, which are specifically incorporated by reference herein.

The m1, m2 and m3 receptors correlate pharmacologically to the M1, M2, and M3 (M2 glandular) receptors, respectively. See Levine, R.R.; Birdsall, N.J.M.; *Subtypes of Muscarinic Receptors IV; Trends in Pharm. Sci.* supplement, Vol. 10; and *Elsevier Trends Journals;* Cambridge UK, 1989, p. VII, which are specifically incorporated by reference herein. The m1 and m3 receptors have been shown to be coupled preferentially to the stimulation of phosphoinositide metabolism, and m2 and m4 receptors have been shown to be coupled preferentially to the inhibition of adenylate cyclase. See Peralta, E. G.; Ashkenazi, A.; Winslow, J. W.; Ramachandran, J.; Capon, D. J., *Nature* 1988, 334, 434; and Hughes, A. R.; Martin, M. W.; Harden, T. K., *Proc. Natl. Acad. Sci USA* 1984, 81, 5680, which are specifically incorporated by reference herein.

Other effector systems, such as voltage-dependent and calcium-dependent potassium channels are coupled to muscarinic receptors. See Adams, P.R.; Brown, D. A.; Constanti, A., *J. Physiol.*, 1982, 332, 223; and Yatani A.; Hamm, H.; Codina, J.; Mazzoni, M. R., Birnbaumer, L.; *Science,* 1988, 241, 828, which are specifically incorporated by reference herein.

In the brain, four genetic subtypes have been localized through hybridization with oligonucleotide probes. See Bonner, T. I; Buckley, N. J.; Young, A. C.; Brann, M. R., *Science* 1987, 237, 527, which is specifically incorporated by reference herein. The working hypothesis that administration of a centrally active, selective muscarinic agonist would relieve the memory loss associated with Alzheimer's disease was deduced from the observed degeneration of presynaptic muscarinic terminals in the nucleus basalis region of these patients. See Fisher, A.; Brandeis, R.; Karton, I.; Pittel, Z.; Dachir, S.; Sapir, M.; Grunfeld, Y.; Levy, A.; and Heldman, E. in "Novel Approaches to the Treatment of Alzheimer's Disease" E. M. Meyer; J. W. Simpkins; J Yamamoto, eds., *Advances in Behavioral Biology*, Vol. 36, Plenum, New York, 1989, pp. 11–16, which is specifically incorporated herein by reference. Subsequent research prompted by this observation has led to the identification of a number of classes of muscarinic agonists. See Baker, R.; Saunders, J.; *Ann. Rep. Medicinal Chem.* 1989, 24, 31, which is specifically incorporated herein by reference.

In addition to the development of new agonists, there is a need to develop more highly selective muscarinic antagonists, both as pharmacological tools and as potential therapeutic agents. For example, the first known m1-selective antagonist, pirenzepine, is useful clinically in the inhibition of gastric acid production. See Hammer, R. B.; Birdsall, N. J. M.; Burgen, A. S. V.; Hulme, E. C.; *Nature* 1980, 283, 90; Hammer, R.; Giachetti, A.; *Life Sci.* 1982, 31, 2991; and Kromer, W.; Gönne, S.; *Int. J. Exp. Clin. Pharmacol.*, 1988, 37 (suppl. 1), 48, which are specifically incorporated herein by reference.

An m3-selective antagonist would be useful in treating airway disease and atonic conditions of the gut and bladder. See Maclagan, J.; Barnes, P.; *Trends Pharamcol. Sci.* 1989 (Suppl. "Subtypes of Muscarinic Receptors IV"), Levine, R.; Birdsall, N. J. M.; pp. 88–92; and Mutschler E.; Feifel, R.; Moser, U.; Tacke, R.; Wess, J.; Lambrecht, G.; *Eur. J. Pharmacol.* 1990, 183, 117, which are specifically incorporated by reference herein. An m4-selective antagonist would be useful in the control of hyperreactivity of smooth muscle. See Mutschler E.; Feifel, R.; Moser, U.; Tacke, R.; Wess, J.; Lambrecht, G.; *Eur. J. Pharmacol.* 1990, 183, 117, which is specifically incorporated by reference herein.

Previous studies by the inventors of structure activity relationships in analogues of the muscarinic agonist oxotremorine utilized a functionalized congener approach, i.e. chemically functionalized chains were incorporated at sites on the pharmacophore that were insensitive to this modification in receptor binding. See Bradbury, B. J.; Baumgold, J.; Jacobson, K. A.; *J. Med. Chem.*, 1990, 33:741–748; and Bradbury, B. J.; Baumgold, J.; Paek, R.; Kammula, U.; Zimmet, J.; Jacobson, K. A.; *J. Med. Chem.*, 1991, 34:1073–1079, which are specifically incorporated by reference herein.

Functionalized congeners in other drug classes have been useful in affinity chromatography to purify receptors, in the synthesis of selective affinity labels, and in prodrug design. See Jacobson, K. A.; Daly, J. D.; *Nucleosides and Nucleotides,* 1991, 10: 1029–1038; and Barone, S.; Churchill, P. C.; Jacobson, K. A.; *J. Pharm. Exp. Therap.* 1989, 250, 79, which are specifically incorporated by reference herein.

The inventors have now extended the functionalized congener approach to analogues of the selective muscarinic antagonists pirenzepine 1 and telenzepine 3.

SUMMARY OF THE INVENTION

The present invention provides novel analogues of pirenzepine and telenzepine which are capable of binding as antagonists to muscarinic receptors. These analogues involve substitution of the distal N-methyl group of pirenzepine or telenzepine. Such analogues result in either intermediate affinity (short chains) or relatively high affinity (long chains of >4 methylenes having terminal amino or acylamino substituents).

The group used for substitution in pirenzepine or telenzepine can be, for example, a propargyl group, a benzyl group, a substituted benzyl group, a hydroxyethyl group, a chloroethyl group, an aminoethyl group, an ω-amino alkyl group, or an N-substituted ω-amino alkyl group. Among this group might be found prosthetic groups for radiolabelling and carriers such as polymers, antibodies, latex microparticles, magnetic particles, etc.

The present invention is also for a process of using such analogues of pirenzepine and telenzepine to synthesize potential affinity probes or affinity columns for muscarinic receptor purification.

Furthermore, the present invention is also for a process of using such analogues for inhibiting gastric acid production in humans by administering a safe and effective amount of said compound.

In addition, the present invention is also related to fluorescent dye probes which result from coupling certain of such analogues with a fluorescent dye moiety.

Furthermore, the invention relates to a process of using such fluorescent dye probes for muscarinic receptor detection, assay, or characterization.

Additional objects and advantages of the invention will be set forth in part in the description which follows, and in part will be obvious from the description, or may be learned from the practice of the invention. The objects and advantages may be realized and attained by means of the instrumentalities and combinations particularly pointed out in the appended claims.

DESCRIPTION OF THE PREFERRED EMBODIMENTS

Chemistry

Figure 1:
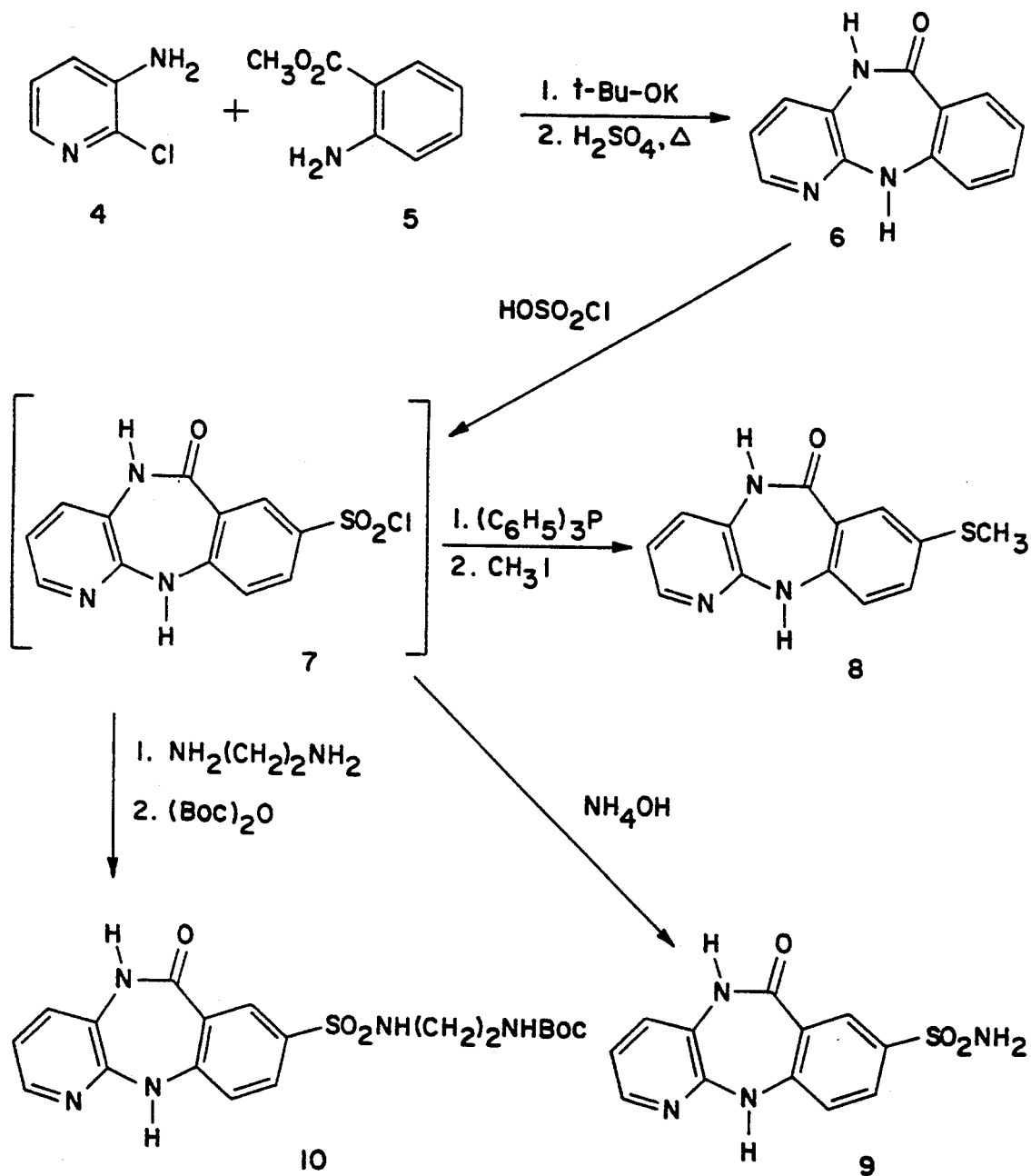
FIGS. 1–6 sets forth reaction schemes I–VI, respectively, illustrating the preparation of various compounds of interest in connection with the present invention.
Figure 2:
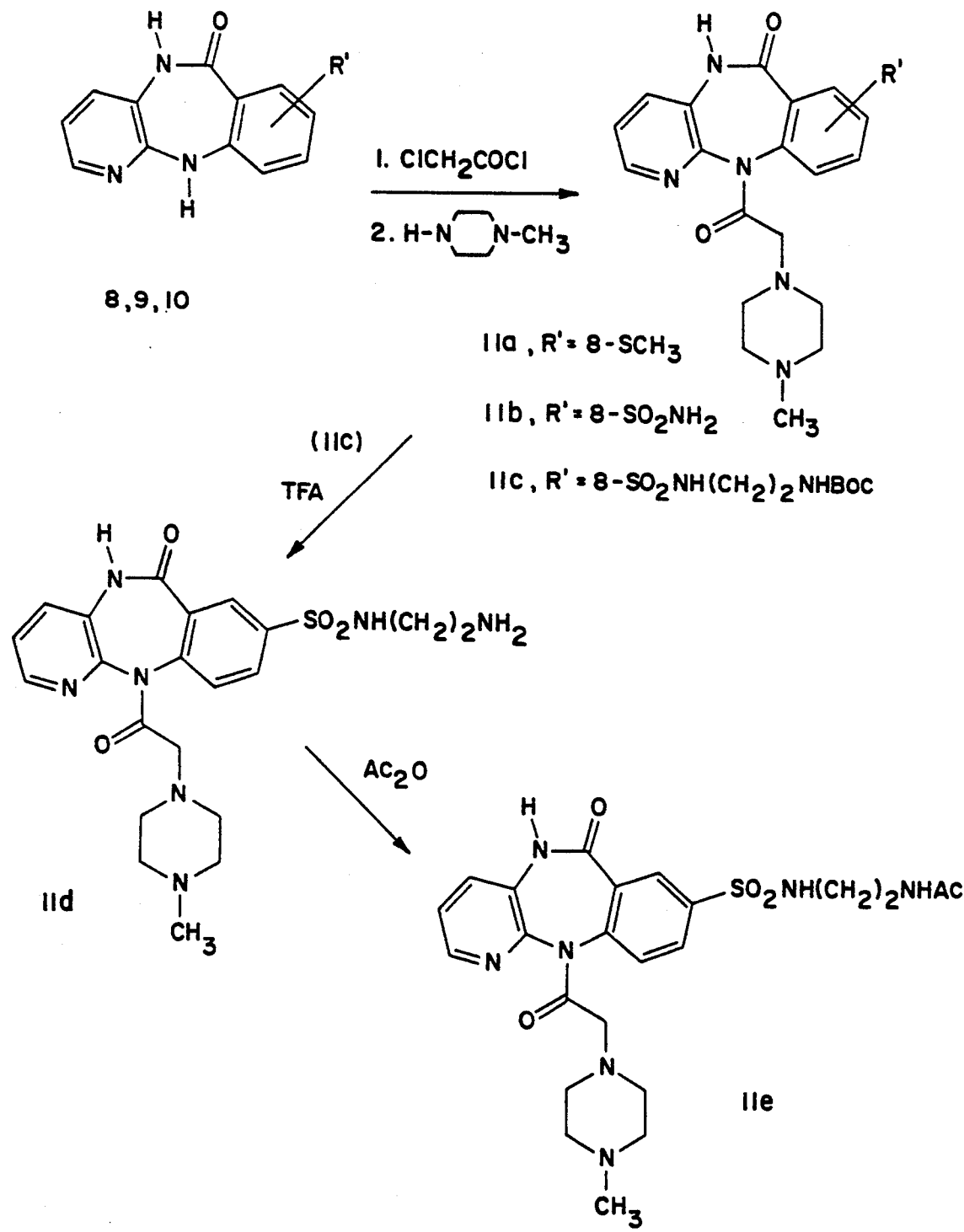
Figure 3:
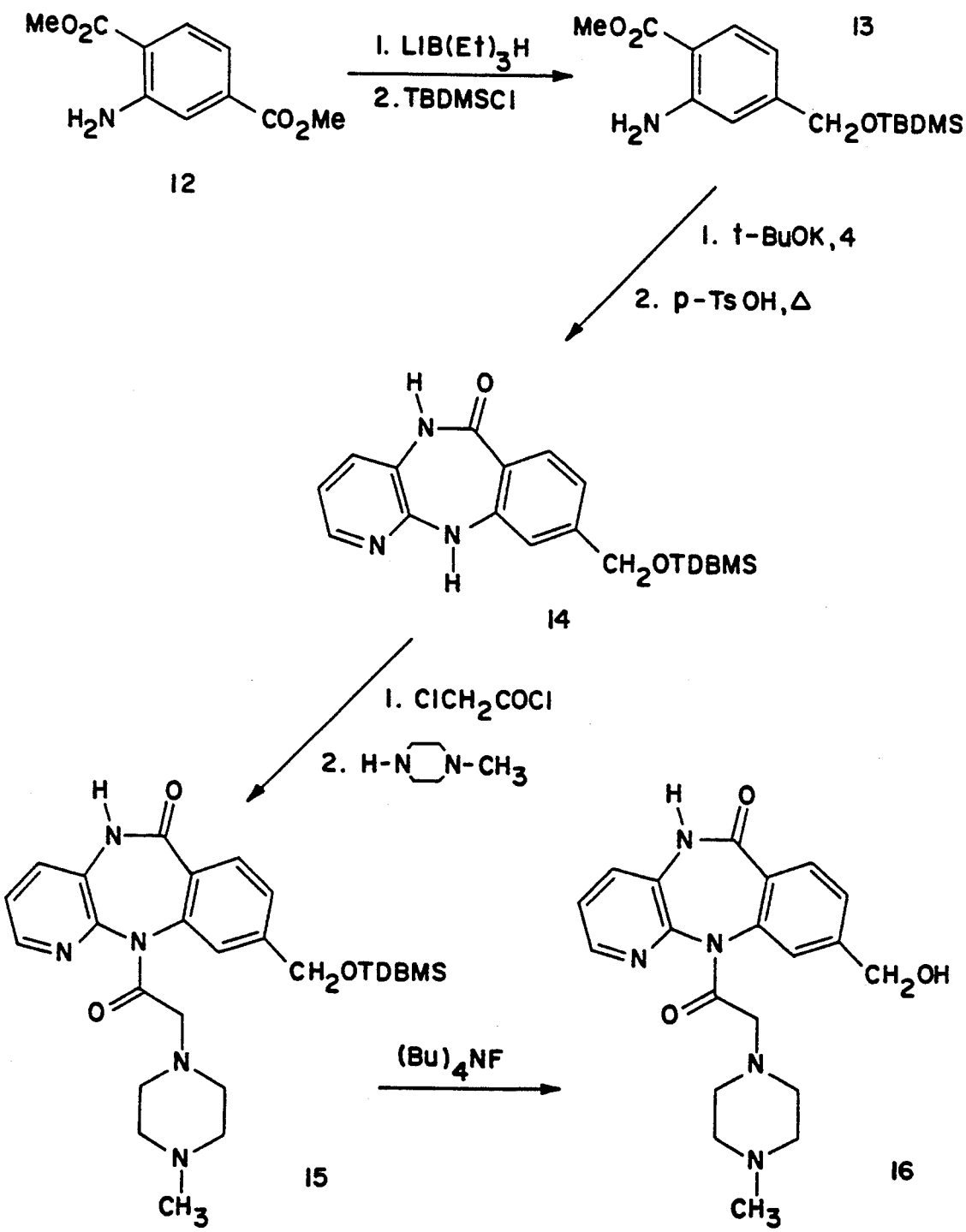
Figure 4:
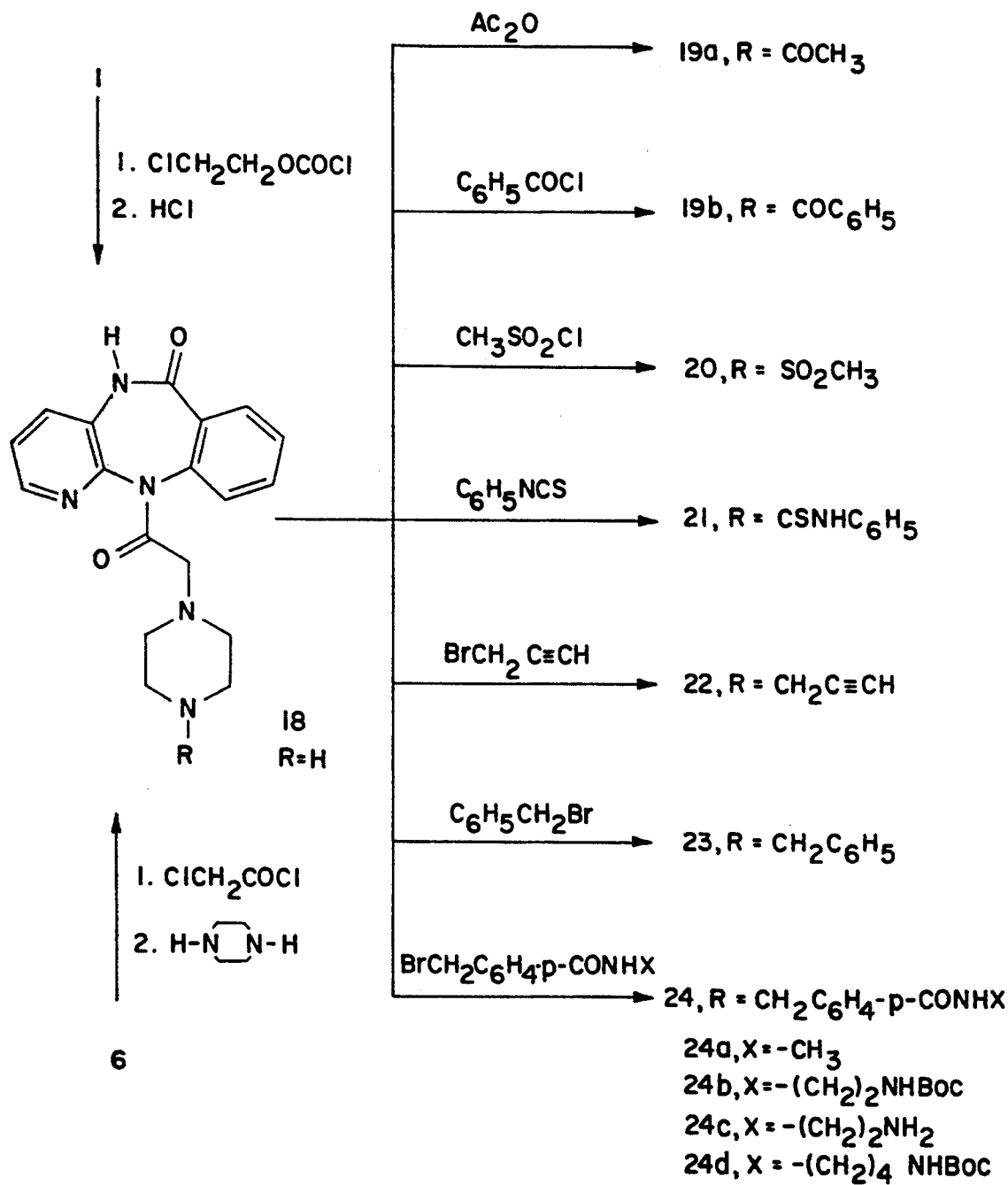
Figure 5:
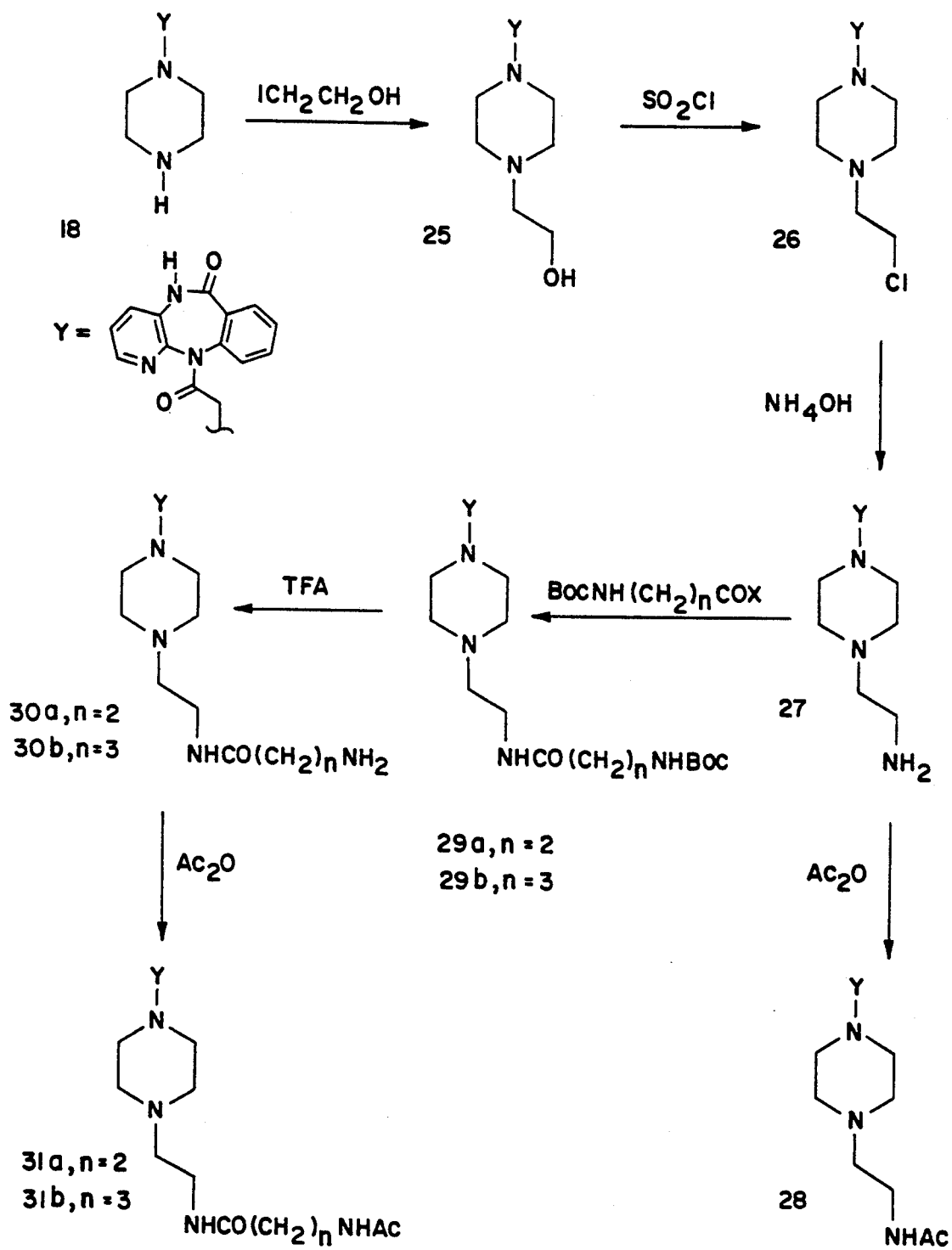
Figure 6:
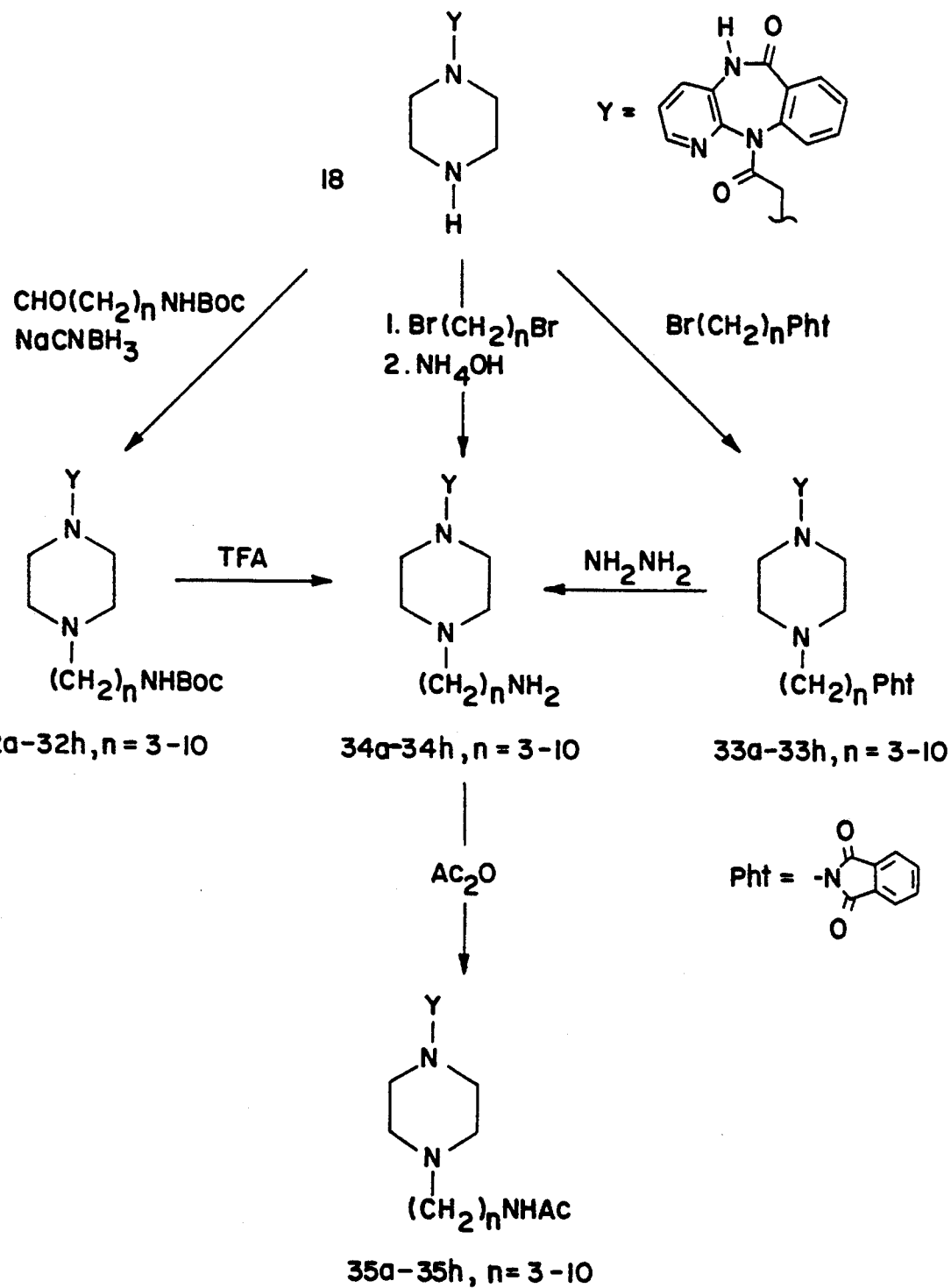
Figure 7:
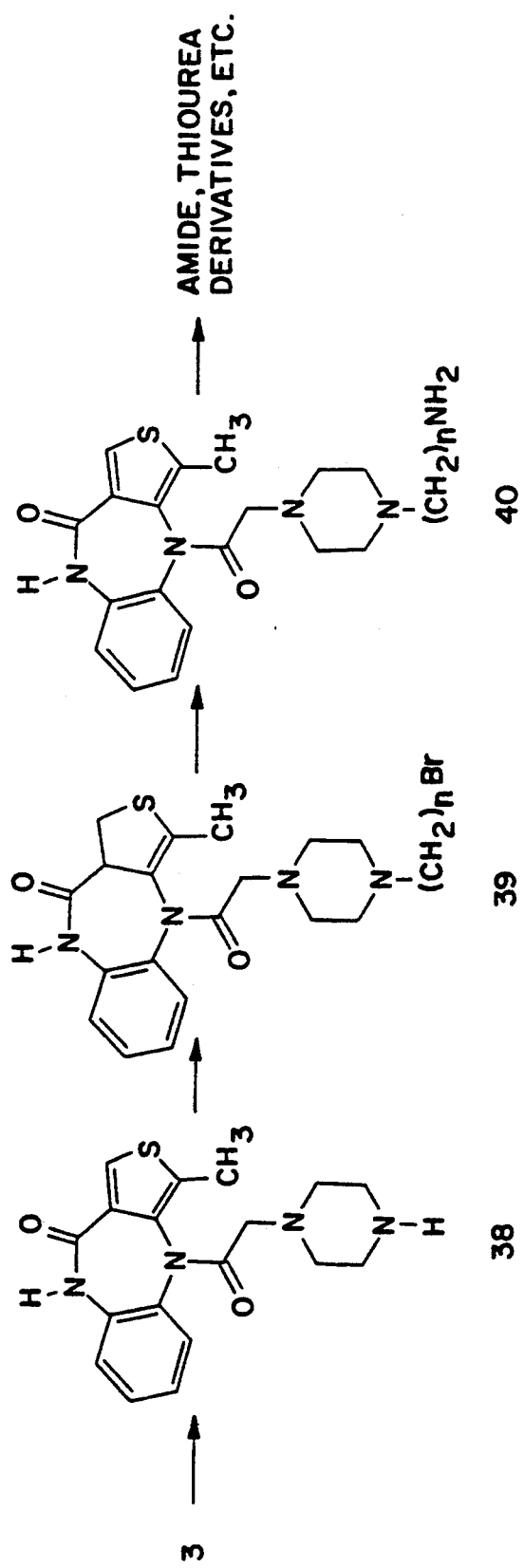
FIG. 7 sets forth a reaction scheme illustrating the synthesis of functionalized congeners of telenzepine.
Figure 8:
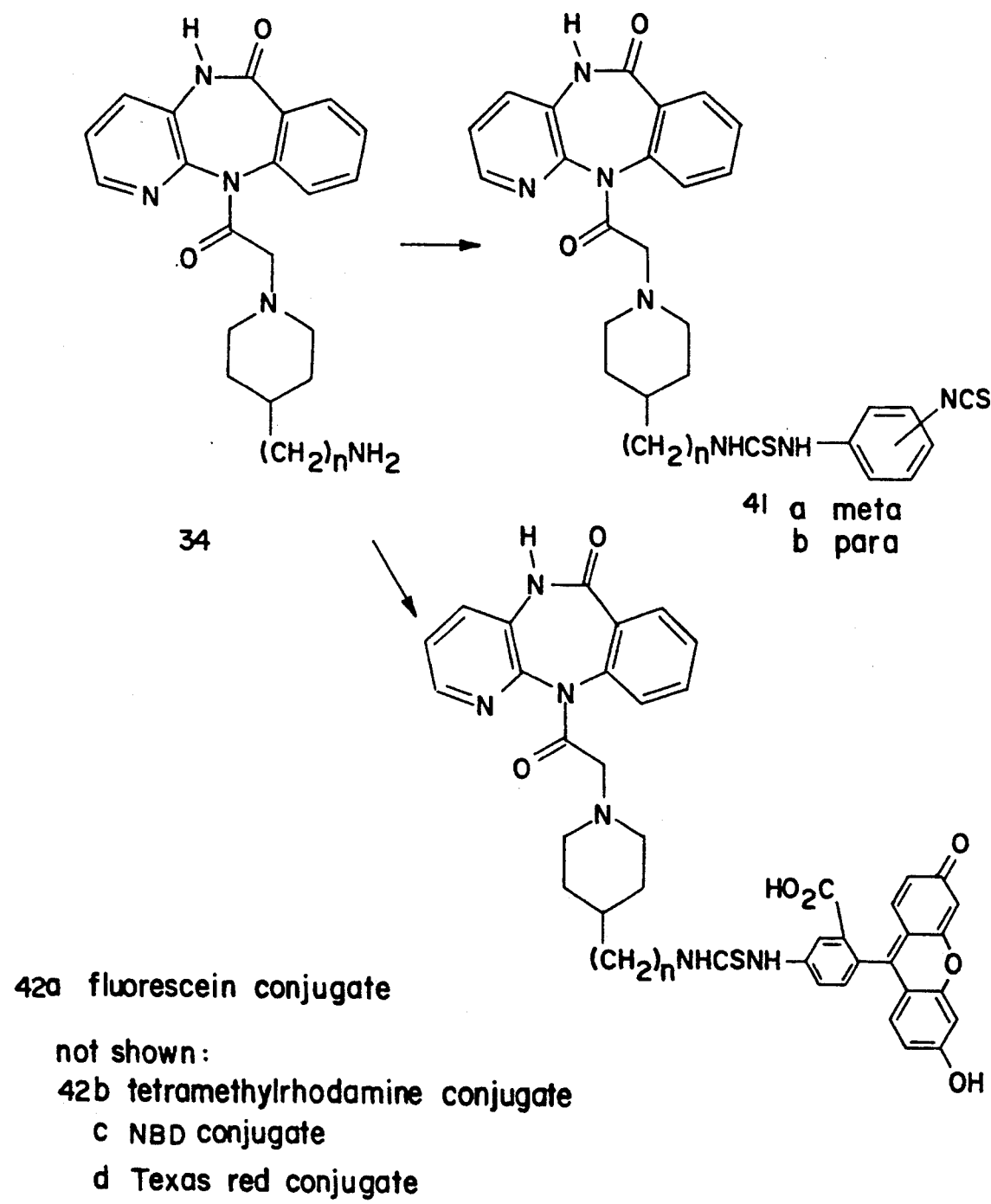
FIG. 8 sets forth a reaction scheme illustrating the synthesis of receptor probes, including irreversible inhibitors and fluorescent probes.

The inventors explored the tricyclic skeleton and the piperazine ring of the pirenzepine and telenzepine molecules as possible sites for the attachment of derivatized chains in making functionalized congeners of pirenzepine and telenzepine. These two regions contain a hydrogen bond acceptor atom (usually a carbonyl oxygen) and a basic nitrogen atom, two key structural elements involved in binding to muscarinic receptors.

Since a number of classes of muscarinic antagonists have major structural differences at the "carbonyl-end" of the ligand, the inventors deduced that there would be sufficient steric freedom for chain attachment on one of the aromatic rings of pirenzepine- See Baker, R.; Saunders, J.; Ann. Rep. Medicinal Chem. 1989, 24, 31, which is specifically incorporated by reference herein.

In addition, a number of muscarinic ligands have been reported in which the basic nitrogen side chain is varied. See Eberlein, W.G.; Trummlitz, G.; Engel, W.W.; Schmidt, G.; Pelzer, H.; Mayer, N.; J. Med. Chem., 1987, 30, 1378; Eberlein, W.G.; Engel, W.W.; Trummlitz, G.; Schmidt, G.; Hammer, R.; J. Med. Chem., 1988, 31, 1169; Eberlein, W. G.; Engel, W.; Mihm, G.; Rudolf, K.; Wetzel, B.; Entzeroth, M.; Mayer, N.; Doods, H. N., Trends Pharm. Sci. 1989, 10 (supplement), 50; and Engel, W. W.; Eberlein, W. G.; Mihm, G.; Hammer, R.; Trummlitz, G.; J. Med. Chem., 1989, 32, 1718, which are specifically incorporated by reference herein.

It appears that structural modifications at the "amine-end" of muscarinic ligands frequently cause major changes in the selectivity profile of the compound- For example, AQ-RA 741 2, which contains the same tricyclic ring system as pirenzepine, is selective for M2 receptors. See Eberlein, W. G.; Engel, W.; Mihm, G.; Rudolf, K.; Wetzel, B.; Entzeroth, M.; Mayer, N.; Doods, H. N.; Trends Pharm. Sci., 1989, 10 (supplement), 50, which is specifically incorporated by reference herein.

On the other hand, certain modifications of pirenzepine in the tricyclic moiety, such as in the more potent antagonist telenzepine 3 preserve selectivity for ml receptors. See Eltze, M.; Gönne, S.; Riedel, R.; Schlotke, B.; Schudt, C.; Simon, W. A.; Eur. J. Pharmacol., 1985, 112, 211, which is specifically incorporated by reference herein.

Pirenzepine and telenzepine analogues containing sites for functionalization and chain extension were synthesized and fully characterized. Analogues containing substituents located on the benzene ring of pirenzepine in the 8-, and 9-positions (Schemes I–III) were included. Small (11a and 16), extended chain (11c-e) or sterically large substituents (15) were prepared.

The position of aromatic substitution was verified by a comparative proton NMR study, which is summarized in Table 2. The C-8 aromatic proton (para-to the amino group) appears at approximately 6.9 ppm from tetramethylsilane in the tricyclic intermediates (6 and 14) and at approximately 7.4 ppm when the amine is acylated, as in 1 and 15. This signal is absent in compounds 8, 9, and 11, which are substituted at the C-8 position.

The tricyclic intermediate 6 was synthesized by published procedures, starting with 3-amino-2-chloropyridine 4 and methyl anthranilate 5 (Scheme I). See Engel, W. W.; Eberlein, W. G.; Mihm, G.; Hammer, R.; Trummlitz, G.; J. Med. Chem., 1989, 32, 1718, which is specifically incorporated by reference herein. Chlorosulfonation of 6 resulted in the formation of the 8-chlorosulfonyl intermediate 7 (not isolated) which was then reduced with triphenylphosphine. See Oae, S.; Togo, H., Bull. Chem. Soc. Jpn., 1983, 56, 3802, which is specifically incorporated by reference herein. The resulting thiol was alkylated to give the corresponding thioether 8.

Prior efforts to substitute pirenzepine 1 directly by a variety of electrophilic reagents (eg. by chlorosulfonation, nitration, chloromethylation) resulted in recovery of unreacted pirenzepine. The extreme inertness of pirenzepine in comparison to 6 can be rationalized partially by the planarity of 6, which enables delocalization of the N-11 electron pair within the benzene ring. Such activation of the benzene ring is not possible in the non-planar, "butterfly" shape of pirenzepine. See Eberlein, W. G.; Engel, W.; Mihm, G.; Rudolf, K.; Wetzel, B.; Entzeroth, M.; Mayer, N.; Doods, H.N., Trends

*Pharm. Sci.* 1989, 10 (supplement), 50, which is specifically incorporated by reference herein. The acylation of the exocyclic amine may also contribute to the relative unreactivity of the tricyclic moiety of pirenzepine.

DETAILED DESCRIPTION OF THE DRAWINGS

Sulfonamides 9 and 10 were also prepared from intermediate 6 according to Scheme I.

Reaction of intermediates 8, 9, and 10 with chloroacetyl chloride and then with N-methylpiperazine gave the 8-substituted pirenzepine analogues 11a, 11b, and 11c, respectively (Scheme II).

Compound 11c was used to prepare analogues 11d and 11e by deprotection with TFA and reaction with acetyl chloride.

The 9-substituted analogues 15 and 16 were prepared from amino terephthalate (12) according to Scheme III.

The carboxymethyl group of compound 12 meta to the amine was selectively reduced with Super-Hydride followed by protection of the hydroxyl group as the t-butyldimethylsilyl ether to give 13. See Ireland, R. E.; Thompson, W. J.; *Tetrahedron Letters,* 1979, 4705; and Ogilvie, K.K.; Beaucage, S. L.; Schifman, A. L.; Theriault, N. Y.; Sadana, K. L.; *Can. J. Chem.*, 1978, 56, 2768, which are specifically incorporated by reference herein.

Intermediate 13 was subsequently condensed with 4 and then cyclized to 14 using a carefully controlled quantity of p-toluenesulfonic acid (<0.1 equiv, pH≈7.0) in order to prevent hydrolysis of the silyl ether. Addition of the 4-methyl-1-piperazinylacetyl side chain to form 15 used the same one-pot procedure as shown in Scheme II.

Removal of the silyl ether with tetrabutylammonium fluoride afforded the final 9-hydroxymethyl analogue of pirenzepine 16. See Ogilvie, K. K.; Beaucage, S. L.; Schifman, A. L.; Theriault, N. Y.; Sadana, K. L.; *Can. J. Chem.*, 1978, 56, 2768, which is specifically incorporated by reference herein.

The 5-position of pirenzepine was derivatized through alkylation of the amide NH, resulting in the N-ethyl and N-6-cyanohexyl derivatives 17a and 17b, respectively. This reaction was carried out at the stage of the tricyclic intermediate 6, followed by elaboration of the N-methylpiperazine side chain, as in Scheme II. See U.S. Pat. No. 3,406,168, (Schmidt), which is specifically incorporated by reference herein.

Although analogues bearing small alkyl substituents at this position were reported in the patent literature to be active, no details concerning selectivity were reported. See Belgian Patents Nos. 867,638 and 867,638 (Thomae), which are specifically incorporated by reference herein.

Much variation in the substitution of the piperazine ring of pirenzepine is tolerated at the muscarinic antagonist binding sites.

The des-methyl analogue of pirenzepine 18, was prepared from compound 1, by treatment with α-chloroethyl chloroformate and a tertiary base, or from 6, by acetylation with chloroacetyl chloride followed by reaction with piperazine. See Hammer, R.; Kaubisch, N.; Kopitar, Z.; Prox, A.; Zimmer, A.; Koss, F. W.; *Therapiewoche* 1977, 27, 1567; and Olofson, R. A.; Martz, J. T.; Senet, J.-P.; Piteau, M.; Malfroot, T., *J. Org. Chem.* 1984, 49, 2081, which are specifically incorporated by reference herein.

Compound 18 served as an intermediate for model compounds derivatized at the 4-position of the piperazine ring (Scheme IV) through acylation (compounds 19-21) or alkylation with propargyl (compound 22), benzyl (compound 23), and 4-substituted benzyl (compounds 24a-d) groups.

Compounds 24a-d offered the possibility of chain extension, dependent on the toleration of an aromatic group close to the piperazine ring.

Straight chain N-alkyl substitution was examined as an alternative to chain extension through a benzyl substituent.

A functionalized ethyl group was introduced at the pirenzepine 4-position through alkylation of 18 with 2-iodoethanol, as shown in Scheme V. The subsequent conversion of the 2-hydroxyethyl derivative 25 to a chloroethyl intermediate, 26, allowed the synthesis of an ethylamino congener 27 and various extended amide derivatives (28-31).

Compound 26 was also of interest as a potential alkylating agent for irreversible inhibition through formation of the aziridinium species. See Wheatley, M.; Hulme, E. C.; Birdsall, N. J. M.; Curtis, C. A. M.; Eveleigh, P.; Pedder, E. K.; Poyner, D.; *Trends Pharm. Sci.* supplement 1988, 19; Ringdahl, B.; Mellin, C.; Ehlert, F.J.; Roch, M.; Rice, K.M.; Jenden, D. J.; *J. Med. Chem.*, 1990, 33,281; and Winkler, J. D.; Thermos, K.; Weiss, B.; *Psychopharmacology,* 1987, 92, 285.; and Hait, W. N.; Glazer, L.; Kaiser, K.; Cross, J.; and Kennedy, K. A., *Mol. Pharmacol.*, 1987, 32, 404, which are specifically incorporated by reference herein.

Homologues of the amino ethyl functionalized congener 27 containing alkyl chains up to 10 methylenes in length were prepared.

An ω-amino side chain was appended to 18 in one of three ways according to Scheme VI: (1) reductive amination using a Boc-protected ω-amino aldehyde to give compound series 32, (2) alkylation with ω-phthaloyl bromides to give series 33, and (3) alkylation with alkyl dibromides and subsequent amination with ammonium hydroxide to give the primary amine analogues 34.

The route utilizing alkyl dibromides was preferred and gave the highest yields. Intermediates 32 and 33 could easily be converted to 34 using TFA or hydrazine, respectively. The primary amines were subsequently acetylated with acetic anhydride to give the N-acetyl derivatives 35. These homologous series were designed to probe the effects of varying chain length and the nature of the distal terminal group on the affinity of the analogue in binding to muscarinic receptors.

Pharmacology

The analogues were screened in binding assays using membranes from cells or tissues containing primarily single subtypes of m1 through m4 muscarinic receptors. Transfected A9L cells were used as a source of homogeneous populations of m1, m3, and m4 receptors. See Jones, S. V.; Barker, J. L.; Buckley, N. J.; Bonner, T. I; Brann, M. R., *Mol. Pharmacol.*, 1988, 34, 421, which is specifically incorporated by reference herein. Rat heart tissue was the source of m2 muscarinic receptors.

The ability of the analogue to displace [$^3$H]N-methylscopolamine ([$^3$H]NMS) was measured, and the results are summarized in Table 1.

As a result of these binding assays, the inventors have found that of all the analogues of pirenzepine and telenzepine synthesized, muscarinic antagonist characteristics were preserved in those analogues which are substituted at the distal N-methyl group.

Specifically, those groups which gave the best results when substituted at this site in pirenzepine and telenzepine were, for example, a propargyl group, a benzyl group, a substituted benzyl group, a hydroxyethyl group, a chloroethyl group, an aminoethyl group, an ω-amino alkyl group, or an N-substituted ω-amino alkyl group.

In contrast, substitution at the 8- and 9-positions of pirenzepine dramatically decreased affinity at all of the muscarinic receptor subtypes. Only the 8-methylthio- and 9-hydroxymethyl analogues 11a and 16, respectively, caused any detectable displacement of [$^3$H]NMS from the receptor.

The inactivity of the aryl-modified analogues was surprising in light of the report of activity of the 8-methyl and 8-ethyl derivatives of pirenzepine. See Engel, W. W.; Eberlein, W. G.; Mihm, G.; Hammer, R.; Trummlitz, G.; *J. Med. Chem.*, 1989, 32, 1718, which is specifically incorporated by reference herein.

In addition, compounds 19-21, in which the most distal nitrogen of the piperazine ring exists in a neutral, acylated form, were totally inactive as muscarinic antagonists. Alkylation of the endocyclic amide, to yield compounds 17a and 17b, resulted in analogues of low affinity.

The only promising strategy for chain functionalization appears to be alkylation of the 4-amino position of the pirenzepine ring.

Among the latter group of derivatives, the shorter chain substituents, eg. the N-propargyl (22) and 2-substituted ethyl derivatives (25, 27, and 28) were weak inhibitors of [$^3$H]NMS binding with $K_i$ values in the vicinity of $10^{-6}$ molar.

In this series, only the chloromethyl derivative 26 retained selectivity for ml receptors. The selectivity ratio for 26 was 4.4-fold in favor of ml versus m2 receptors, compared to a ratio of 21 for pirenzepine 1. Telenzepine 3 has a ratio of 25 in favor of m1 versus m2 receptors. The N-benzyl derivative 23 was non-selective for ml versus m2 receptors.

Although larger sterically than the propargyl derivative 22, compound 23 had greater affinity at ml and m2 muscarinic receptors. This indicated that there may be a region on the receptor accessory to the pharmacophore binding site which favors a hydrophobic group.

This observation prompted the synthesis of compounds 24a-d, in which functionalized chains were extended via a carboxylic group at the para-position of 23. However a decrease in binding affinity was observed in this series. Amino acid derivatives (29-31, a and b) of the ethylamino congener indicated a loss in potency as the chain was extended by amide bond formation.

There was no apparent correlation in receptor affinity among charged (amino group, compound 30), small neutral (acetylamino, compound 31), and neutral, hydrophobic (t-butyloxycarbonylamino, compound 29) terminal substituents.

The chloroethyl mustard derivative 26 was examined as a potential irreversible inhibitor of muscarinic receptors. A similar mustard derivative of the dopamine receptor antagonist fluphenazine has been reported to be an irreversible inhibitor of D1 and D2 dopamine receptors and of calmodulin. See Winkler, J. D.; Thermos, K.; Weiss, B.; *Psychopharmacology*, 1987, 92, 285; and Hait, W. N.; Glazer, L.; Kaiser, K.; Cross, J.; and Kennedy, K. A., *Mol. Pharmacol.*, 1987, 32, 404, which are specifically incorporated by reference herein.

At muscarinic receptors, propylbenzylcholine mustard apparently binds covalently to an aspartyl residue at the ligand binding site. See Wheatley, M.; Hulme, E. C.; Birdsall, N. J. M.; Curtis, C. A. M.; Eveleigh, P.; Pedder, E. K.; Poyner, D.; *Trends Pharm. Sci.* supplement 1988, 19, which is specifically incorporated by reference herein.

A chloroethyl mustard derivative of the muscarinic agent McN-A-343 has also been reported. See Ringdahl, B.; Mellin, C.; Ehlert, F. J.; Roch, M.; Rice, K. M.; Jenden, D.J., *J. Med. Chem.*, 1990, 33, 281, which is specifically incorporated by reference herein. The active alkylating agent is thought to be the aziridinium species, which forms spontaneously in neutral or slightly basic aqueous medium.

To assay for irreversible inhibition in rat brain membranes, Scatchard analyses before and after treatment of the membranes with 26 were compared. Even a very high of radioligand binding. $K_d$ and $B_{max}$ values at binding sites concentration of 26 failed to effect irreversible inhibition for [$^3$H]NMS were found to be 357 pM and 0.74 pmol/mg protein, respectively. Preincubation with a concentration of 1.0 mM compound 26 produced no change in the $K_d$ and $B_{max}$ values. Thus, 26 is a not an irreversible inhibitor of ml receptors.

The lack of irreversible inhibition in spite of high binding affinity of 26 suggests that there is no nucleophilic group at the binding site in close proximity to the aziridine ring.

Among straight chain terminally-functionalized N-alkyl derivatives, a marked enhancement of affinity at muscarinic receptors was observed as the number of methylene groups was increased from 2 to 10. With seven or more methylene units, the $K_i$ values for the free amines (34e-h) were below 100 nanomolar. Moreover, for the intermediate chain lengths (3-6 methylenes), analogues having large, hydrophobic groups at the terminal position, eg. phthaloyl amino (33) and t-butyloxycarbonylamino (32d), were more potent than the corresponding free amines (34).

In the series having longer chain lengths such as nine and ten methylene units, derivatives bearing a free amino group (34g and 34h) had higher affinities than the corresponding derivatives with the small neutral acetylamino terminal group (35g and 35h). An aminodecyl derivative 34h had $K_d$ values of less than 20 nM at both ml and m2 receptors.

The free amino derivative with five methylenes 34c displayed a 5-fold selectivity of ml versus m2 receptors.

The other chain extended primary amino derivatives were non-selective, as were the small methyl-modified pirenzepine analogues, such as 22.

Compounds 36 and 37 were further analogues of compound 34h, designed with amine substituents similar to the terminal groups of the m2 selective antagonists AQ-RA-741 and methoctramine, respectively, and however displayed ml-selectivity. See Eberlein, W. G.; Engel, W.; Mihm, G.; Rudolf, K.; Wetzel, B.; Entzeroth, M.; Mayer, N.; Doods, H. N., *Trends Pharm. Sci.* 1989, 10 (supplement), 50; Melchiorre, C.; Cassinelli, A.; Quaglia, W., *J. Med. Chem.*, 1987, 30, 201; and Melchiorre, C.; Cassinelli, A.; Angeli, P.; Giardina, D.; Gulini, U.; Quaglia, W., *Trends Pharm. Sci.* supplement 1988, 55, which are specifically incorporated by reference herein.

A functionalized congener approach to drug design has been shown to be useful for enhancing potency and selectivity of ligands that bind to extracellular receptor sites, in affinity chromatography or affinity labeling of receptors, and in prodrug design. See Olah, M. E.; Jacobson, K. A.; Stiles, G. L., *Arch. Biochem. Biophys.* 283, 440; Stiles, G. L.; Jacobson, K.A.; *Mol. Pharmacol.* 1988, 34, 724; and Barone, S.; Churchill, P. C.; Jacobson, K. A.; *J. Pharm. Exp. Therap.* 1989, 250, 79, which are specifically incorporated by reference herein.

A starting point for this approach is the identification of insensitive sites on the drug molecule, suitable for covalent attachment of a chemically functionalized chain.

The chain may be modified in a stepwise fashion to optimize biological, physical, and spectroscopic properties, resulting in high affinity receptor probes. See Jacobson, K. A.; Daly, J. D.; *Nucleosides and Nucleotides,* 1991, 10: 1029–1038, which is specifically incorporated by reference herein. For example, an amine functionalized adenosine antagonist has been converted into an isothiocyanate-bearing affinity label for A1 adenosine receptors. See Stiles, G. L.; Jacobson, K. A.; *Mol. Pharmacol.* 1988, 34,724, which is specifically incorporated by reference herein.

Fluorescent and biotinylated probes for adenosine receptors have also been prepared using this approach. See Jacobson, K. A.; Daly, J. D.; *Nucleosides and Nucleotides,* 1991, 10: 1029–1038, which is specifically incorporated by reference herein.

The inventors have previously explored sites for functionalization of the muscarinic agonist, oxotremorine, resulting in analogues that mostly lack agonist activity, but retain receptor affinity. See Bradbury, B. J.; Baumgold, J.; Jacobson, K. A.; *J. Med. Chem.,* 1990, 33:741–748, which is specifically incorporated by reference herein.

The approach is now extended to muscarinic antagonists. A structurally versatile class of high affinity receptor probes would be useful for characterizing muscarinic receptors.

Recently, an isothiocyanate derivative of aprophen was reported to be an irreversible antagonist for muscarinic receptors. See Newman, A. H.; Covington, J.; Oleshansky, M.; Jackson, B. W.; Weissman, B. A.; Leader, H.; Chiang, P. K., *Biochem. Pharmacol.* 1990, 40, 1357, which is specifically incorporated by reference herein.

To summarize the effects on receptor affinity of incorporating a functionalized chain in pirenzepine: Chain substitution at the C-8 or C-9 position essentially abolishes muscarinic receptor binding, whereas substitution of the endocyclic amide NH (position 5) results in weak affinity. Alkyl substitution of the distal N-methyl group of pirenzepine results in either intermediate affinity (short chains) or relatively high affinity (long chains of >4 methylenes having terminal amino or acylamino substituents). Acylation of the distal piperazine amino group abolishes receptor binding.

This study demonstrates clearly that the receptor affinity within a series of analogues may be increased using a functionalized congener approach, although most of the analogues synthesized did not distinguish among muscarinic receptor subtypes.

For example, relative to short chain analogues (eg. 33 a and b and 34 a and b) there was a constant increase in the affinity as the chain length of the straight alkyl derivatives was increased, at least until ten methylenes. The increasing hydrophobicity may be a factor in this trend of higher affinity as the chain is lengthened, but it is not sufficient to account for all of the differences.

Among free amine derivatives, a relatively large jump in potency was achieved at the point of seven methylene units. The decyl amino analogue 34h was the most potent in the series of primary amines, which suggested that longer straight alkyl chains may result in even higher affinities.

Although 34h is non-selective, related secondary and tertiary amine analogues, 36 and 37, were selective for m1 receptors by factors of 5 and 7, respectively, suggesting that further elaboration of the chain structure may lead to greater selectivity.

In general, the affinity of the more potent analogues of pirenzepine compared well with that of pirenzepine, although the m1-selectivity characteristic of pirenzepine was diminished or lost completely. For example, compound 37 was 9-fold and 29-fold more potent than pirenzepine at m1 and m2 receptors, respectively.

There is no explanation for the relatively weak activity of the analogues in which the chain contains an amide link. Compounds 29a and 32d both contain straight chains of six atoms between the piperazine amine and the t-butyloxycarbonylamino group, and therefore may possibly attain similar conformations in the extended state, yet they differ in affinity by factors of 360 at m1 receptors and 280 at m2 receptors.

Overall hydrophobicity (substitution of an amide bond for two methylene groups adds approximately 2 log P units) is not a sufficient explanation, as evidenced by the inactivity of the lipophilic Boc derivative 29a, versus the corresponding amine 30a. Conformational factors or possibly distal sites of interaction between the antagonists and muscarinic receptor molecules remain as possible explanations. Other muscarinic ligands are thought to span distances on the receptor protein while in the bound conformation.

By analogy, the m2-selective muscarinic antagonist methoctramine in the bound state has been proposed to bridge two vicinal receptor sites. See Melchiorre, C.; Cassinelli, A.; Quaglia, W., *J. Med. Chem.,* 1987, 30, 201; and Melchiorre, C.; Cassinelli, A.; Angeli, P.; Giardina, D.; Gulini, U.; Quaglia, W., *Trends Pharm. Sci.* supplement 1988, 55, which are specifically incorporated by reference herein. A study of the affinity as a function of chain length separating two 2-methyloxybenzylamino pharmacophores indicated that there was an optimal chain length, which consisted of 24 atoms. Although in the experiments performed by the inventors, no evidence was found to indicate that an optimal chain length has been reached, there is a leveling trend in the affinity beyond six methylenes.

In summary, it has been found that of all the analogues of pirenzepine and telenzepine synthesized and tested by the inventors, muscarinic antagonistic characteristics were preserved in those analogues which are alkyl substituted at the distal N-methyl group.

Specifically, those groups which gave the best results when substituted at this site in pirenzepine and telenzepine were, for example, a propargyl group, a benzyl group, a substituted benzyl group, a hydroxyethyl group, a chloroethyl group, an aminoethyl group, an $\omega$-amino alkyl group, or an N-substituted $\omega$-amino alkyl group.

In conclusion, the invention relates to a site on the pirenzepine or telenzepine molecules for chain derivatization which provides the opportunity to synthesize potential spectroscopic or other affinity probes, or affinity columns for receptor purification. These functionalized congeners may also be covalently coupled to "carriers" such as polymers, antibodies (for targeting), latex micropartices, magnetic particles, etc., since the terminal functional group is at an insensitive site in receptor binding, i.e. conjugates of these drugs are designed to retain biological activity.

Furthermore, the invention provides a way to alter the overall hydrophobicity of the molecules, which might favorably affect the biodistribution of the analogues.

The loss of selectivity in the pirenzepine derivatives may yet be overcome through further structure-activity studies. Similar chain derivatization may prove to be useful for other members of the pyridobenzodiazepine class and closely related classes of muscarinic antagonists.

In addition to the functional groups specifically mentioned in the Examples below, other functional groups can also be alkyl substituted in the distal N-methyl group of pirenzepine and telenzepine to form analogues which preserve muscarinic antagonist characteristics.

For example, other groups that can be substituted are: $-(CH_2)_n-NHCSNH-aryl$, $-(CH_2)_n-NHCSNH-(C_6H_4)m-NCS$, $-(CH_2)_n-NHCSNH-(C_6H_4)p-NCS$, $-(CH_2)_n-NHCO-alkyl$, $-(CH_2)_n-NHCO-aryl$, $-(CH_2)_n-NH-X-biotin$, $-(CH_2)_n-N-H-radiolabelling$ prosthetic group, or $-(CH_2)_n-N-H-carrier$, where n is from 2 to 10, X is a spacer, alkyl is $C_nH_{2n+1}$, and aryl is a benzene ring or a derivative of a benzene ring such as naphthalene, phenanthrene, anthracene, etc.

EXAMPLES

In the Examples below, 1H NMR spectra were recorded using a Varian XL-300 FT-NMR spectrometer and all values are reported in parts per million (ppm, δ) downfield from tetramethylsilane (TMS).

For kinetic studies, a Varian 500 MHz spectrometer was used. Chemical ionization MS using ionized NH3 gas were recorded using a Finnigan 1015D mass spectrometer modified with EXTREL electronics. Fast atom bombardment MS was carried out on a Jeol JMS-SX102 mass spectrometer.

Thin-layer chromatography (TLC) analyses were carried out using EM Kieselgel 60 F254, DC-Alufolien 200μ plates and were visualized in an iodine chamber and/or with 1% ninhydrin in ethanol. Silica gel columns used MN-Kieselgel 60 230-400 mesh silica gel. Elemental analyses were performed by Atlantic Microlabs, Inc., Atlanta, Ga.

The term in vacuo refers to a water aspirator (15-30 mm Hg) rotary-evaporator. Percent yields are rounded to the nearest whole number. Pirenzepine hydrochloride and telenzepine hydrochloride were obtained from Research Biochemicals, Inc. (Natick, Mass.).

EXAMPLE 1

Synthesis of 5,11-Dihydro-8-chlorosulfonyl-6H-pyrido[2,3-b][1,4]benzodiazepine-6-one (7)

Compound 6 (1.04 g, 4.9 mmol) was added in small portions to 6 mL of chlorosulfonic acid. The mixture was heated to 65°-70° C. for 30 min, then poured over 300 g of ice. A precipitate consisting of the 8-chlorosulfonyl derivative (7) was collected by filtration and immediately dissolved in the solvent used for the preparation of compounds 8, 9, and 10.

EXAMPLE 2

Synthesis of 5,11-Dihydro-8-methylthio-6H-pyrido [2,3-b][1,4]benzodiazepine-6-one (8)

Intermediate 7, freshly prepared from 6 (0.5 g, 2.4 mmol), was reduced with triphenylphosphine (2.8 g, 11.0 mmol) in dioxane (20 mL) for 2 h at 90° C. See Oae, S.; Togo, H., *Bull. Chem. Soc. Jpn.*, 1983, 56, 3802, which is specifically incorporated by reference herein. The crude 8-thio-derivative was quenched (10 min, 25° C.) with excess methyl iodide (0.5 mL, 8.0 mmol) and crystallized from toluene to yield 50 mg (8% from 6) of 8 as a waxy solid: 1H NMR (CDCl3) δ 2.40 (s, 3 H, CH3), 6.25 (br s, 1 H, NH), 6.66 (d, J =8.3, 1 H), 6.86 (dd, J =7.7, 4.4 Hz, 1 H), 7.06 (d, J =8.2 Hz, 1 H), 7.24 (dd, J =8.3, 2.3 Hz, 1H), 7.79 (d, J =2.3 Hz, 1 H), 7.91 (d, J =4.5 Hz, 1 H); MS (CI/NH3) m/e 258 (MH+, base), 243,211, 113.

EXAMPLE 3

Synthesis of 5,11-Dihydro-8-sulfonamido-6H-pyrido [2,3-b][1,4]benzodiazepine (9)

Intermediate 7, freshly prepared from 6 ( 1.0 g, 4.7 mmol), was dissolved in 25 mL of DMF and 25 mL of NH4OH. The mixture was stirred at room temperature for 20 min and the precipitate was filtered, washed with water, and dried to yield 0.76 g (55%) of 9 as a white waxy solid: 1H NMR (DMSO-d6) δ 7.01 (dd, J =7.7, 4.6 Hz, 1 H), 7.23 (d, J =7.6 Hz, 1 H), 7.25 (d, J =8.5 Hz, 1 H), 7.73 (dd, J =8.5, 2 Hz, 1 H), 7.94 (d, J =4.6 Hz, 1 H), 8.23 (d, J =2 Hz, 1 H), 9.15 (s, 1 H, NH), 10.10 (s, 1 H, NH); MS (CI/NH3) m/e 291 (MH+, base), 232.

EXAMPLE 4

Synthesis of 5,11-Dihydro-8-[2(N-Boc-amino)ethylsulfonamido]-6H-pyrido[2,3-b][1,4]benzodiazePine-6-one (10)

Intermediate 7, freshly prepared from 6 (1.04 g, 4.9 mmol), was dissolved in 6 mL of ethylenediamine and stirred for 15 min at room temperature. The crude product was precipitated by addition of excess petroleum ether, washed several times with ether and water, and dried overnight to yield 794 mg (48.6%) of 5,11-dihydro-8-[2-aminoethylsulfonamido]-6H-pyrido[2,3-b][1,4]benzodiazepine-6-one as a white crystalline solid: mp >250° C. (dec); 1H NMR (DMSO-d6) δ 2.51 (t, J =6.3 Hz, 2 H), 2.72 (t, J =6.3 Hz, 2 H), 6.98 (dd J =5.0, 7.8 Hz, 1 H), 7.25 (d J =8.5 Hz, 1 H), 7.32 (d, J =7.8 Hz 1 H), 7.69 (dd, J =8.5, 1.5 Hz, 1 H), 7.92 (d, J =5.0 Hz, 1 H), 8.16 (d, J =1.5 Hz, 1 H), 9.19 (s 1 H); MS (CI/NH3) m/e 334 (MH+), 291, 212, 180.

This intermediate ( 3.4 g, 10 mmol ) was then dissolved in 30 mL of DMF and triethylamine (1.0 g, 10 mmol) and di-tert-butyldicarbonate (2.4 g, 11 mmol) were added. The mixture was allowed to stir for 1 h before it was poured into 300 mL of water and filtered. The filtrate was washed with water and dried in vacuo to yield 3.9 g (90%) of 10 as a white solid: mp 195°-198 ° C.: 1H NMR (DMSO-d6) δ 1.34 (s, 9 H, (CH3)3), 2.70 (m, 2 H, CH2), 2.90 (m, 2 H, CH2), 6.74 (br s, 1 H, NH), 7.00 (dd, J =7.7, 4.6 Hz, 1 H), 7.23 (d, J =7.6 Hz, 1 H), 7.3 (d, J =8.5, 1H), 7.55 (br t, 1 H, NH), 7.68 (dd, J =8.6, 2.3 Hz, 1H), 7.92 (dd, J =4.7, 1.3, 1 H), 8.15 (d, J =2.2 Hz, 1 H); MS (CI/NH3) m/e 451 (MH+), 161 (base), 334, 212, 104.

GENERAL PROCEDURE A

Reaction of Substituted 5,11-Dihydro-6H-pyrido[2,3-b][1,4]benzodiazepine-6-ones with 2-Chloroacetylchloride and N-Methylpiperazine The substituted 5,11-dihydro-6H-pyrido[2,3-b][1,4]benzodiazepine-6-one (compounds 6, 8, 9, 10, 15, or 36) (1 equiv) was dissolved in dioxane containing triethylamine (2 equiv) and 2-chloroacetylchloride (1.5 equiv) and refluxed for 5 h (complete by TLC). The solution was cooled to room temperature, N-methylpiperazine (5 equiv) was added, and the solution was refluxed for 1 h. After cooling, the solvent was removed in vacuo and the crude mixture was purified on a silica gel column (20–95% CHCl3, 5–80% of 10/1 MeOH/NH4OH). This procedure was used to make compounds 11a, 11b, 11c, 15, and 36. A modified procedure was used to prepare compound 18 using piperazine in place of N-methylpiperazine.

EXAMPLE 5

Synthesis of 5,11-Dihydro-8-methylthio-11-[4-methyl-1-piperazinyl) acetyl]-6H-pyrido [2,3-b][1,4]benzodiazepine-6-one (11a)

Compound 11a was made from 8 according to general procedure A and was crystallized from methanol ($\approx$68%); mp 205 °C.(dec): 1H NMR (CDCl3) δ 2.30 (s, 3 H, NCH3), 2.52 (s, 3 H, SCH3), 3.25 (d, J =14.0 Hz, 1 H), 3.50 (m, 1 H), 7.31 (dd, J =7.9, 3.2 Hz, 1 H), 7.47 (dd, J =8.5, 2.2 Hz, 1H), 7.53 (d, J =8.5 Hz, 1 H), 7.61 (dd, J =7.9, 1.2 Hz, 1 H), 7.78 (d, J =2.1 Hz, 1 H) ; MS (CI/NH3) m/e 398 (MH+, base), 241, 113.

EXAMPLE 6

Synthesis of 5,11-Dihydro-8-sulfonamido-11-[4-methyl-1-piperazinyl)acetyl]-6H-pyrido[2,3-b][1,4]benzodiazepine-6-one (11b)

Compound 11b was made from 9 according to general procedure A: 1H NMR (CD3OD) δ 2.21 (s, 3 H, CH3), 2.10–2.50 (m, 8 H), 3.10 (m, 1 H), 3.61 (m, 1 H), 7.44 (dd, J =8.0, 4.5 Hz, 1 H), 7.65 (m, 1 H), 7.70 (m, 1 H), 8.11 (dd, J =8.0, 2.2 Hz, 1 H), 8.28 (br s, 1 H), 8.38 (br s, 1 H); MS (CI/NH3) m/e 431 (MH+, base), 384, 308, 113.

EXAMPLE 7

Synthesis of 5,11-Dihydro-8-[2(N-Boc-amino) -4-ethylsulfonamido]-11- [4 -methyl-l-piperazinylacetyl ]-6H-pyrido[2,3-b][1,4]benzodiazepine-6-one (11c)

Compound 11c was made from 10 according to general procedure A and was purified by crystallization of its oxalate salt from isopropanol: mp 210–215 ° C.; (dec). 1H NMR (D2O) δ 1.28 (s, 9 H, (CH3)3), 2.82 (s, 3 H, CH3), 2.40–3.60 (m, 16 H), 7.60 (m, 1 H), 7.70–7.95 (m, 2 H), 8.18 (m, 1 H), 8.29–8.45 (m, 2 H). Free base: (CDCl3) δ 1.41 (s, 9 H, (CH3)3), 2.18 (S, 3 H, CH3), 2.10–2.56 (m, 8 H), 3.10–3.35 (m, 6 H), 7.35 (dd, J =8.0, 4.4, Hz, 1 H), 7.69 (dd, J =7.9, 1.2 Hz, 1 H), 7.76 (d, J =8.5 Hz, 1 H), 8.07 (dd, J =8.4, 2.3 Hz, 1 H); MS (CI/NH3) m/e 575 (MH+), 518, 500, 476 (base), 431, 241.

GENERAL PROCEDURE B

Removal of N-Boc protecting group. Excess TFA was added slowly to the neat Boc-protected amine derivative and the reaction was stirred for 1 h or until complete by TLC. The excess TFA was removed under a stream of N2, and the residue was dried for 24 h at 50 ° C. under high vacuum (0.1 mm Hg) to yield the TFA salts. For spectral analysis, an aliquot was neutralized with 2M Na2CO3 solution, extracted into EtOAc (3 X equal volume), dried over Na2SO4, and evaporated in vacuo. This procedure was used to make compounds 11d, 24c, 30a, 30b.

EXAMPLE 8

Synthesis of 5,11-Dihydro-8-[2-aminoethylsulfonamido]-11-[4-methyl-1-piperazinyl)acetyl]-6H-pyrido[2,3-b][1,4]benzodiazepine-6-one (11d)

Compound 11d was made from 11c using general procedure B: mp 155°–158° C.; 1H NMR (D2O) oxalate salt δ 2.92 (s, 3 H, CH3), 2.60–3.65 (m, 14 H), 7.60 (m, 1 H), 7.81 (br d, J =8.4 Hz, 1 H), 7.85 (br d, J =8.1 Hz, 1 H), 8.32 (br s, 1 H), 8.38 (d, J =4.1 Hz, 1 H); MS (CI/NH3) m/e 474 (MH+), 384, 352, 244, 241 (base).

GENERAL PROCEDURE C

N-Acetylation

The amine intermediate was dissolved in CH3CN and 1.5 equivalents of triethylamine and 1.2 equivalents of acetic anhydride were added. After 15 min, or when judged complete using TLC, the CH3CN was removed under a stream of N2. The residue was dissolved in EtOAc, and washed with 2M Na2CO3 saturated with NaCl (3 X equal volume). The organic phase was dried over Na2SO4 and all volatile materials were removed in vacuo. The crude product was chromatographed (CHCl3/CH3OH/NH4OH, 40/10/1) to give the corresponding N-acetylamino compound (11e, 19a, 28, 31a, 31b, 35a–35h).

EXAMPLE 9

Synthesis of 5,11 Dihydro-8 [2(N-acetyl)ethylsulfonamido]11-[(4-methyl-l-piperazinyl)acetyl]-6H-pyrido[2,3-b][1,4]benzodiazepine-6-one oxalate (11e)

Compound 11e was made from 11d using general procedure C. The oxalate salt was crystallized from methanol: mp 190–195 ° C.; 1H NMR (D2O) δ 1.69 (s, 3 H, CH3), 2.88 (s, 3 H, CH3), 2.60–3.60 (m, 14 H), 7.60 (m, 1 H), 7.76 (br d, J =8.3 Hz, 1 H), 7.85 (br d, J =7.8 Hz, 1 H), 8.16 (br s, 1 H), 8.30 (s, 1 H), 8.40 (m, 1 H); MS (CI/NH3) m/e 516 (MH+), 243, 212, 159, 103 (base).

EXAMPLE 10

Synthesis of Methyl-2-amino-4-(dimethyl-t-butylsilyloxy) methyl benzoate (13)

Methyl 2-amino-4-carbomethoxybenzoate (12, 4.0 g, 19.0 mmol) was dissolved in dry THF and cooled in a dry ice-acetone bath under an inert atmosphere. Superhydride (65 mL, 1.0M) was added slowly by syringe over a period of 1 h. A small aliquot of the solution was quenched with water and purified on a silica gel column to yield methyl 2-amino-4-hydroxymethylbenzoate as a white solid: mp. 100°–102 ° C. 1H NMR (CDCl3) δ 3.82

(s, 3 H, CH3), 4.64 (s, 2 H, CH2), 5.82 (br s, 2 H, NH2), 6.58 (d, J =8.1 Hz, 1H), 6.66 (br s, 1 H), 7.81 (d, J =8.0 Hz, 1 H); MS (CI/NH3) m/e 182 (MH+, base), 167, 150.

Compound 13 was prepared from the remaining solution above using tert-butyldimethylchlorosilane. See Ireland, R. E.; Thompson, W. J., *Tetrahedron Letters*, 1979, 4705, which is specifically incorporated by reference herein. A small amount of the resulting solution was purified on a silica gel column to yield pure 13: 1H NMR (CDCl3) δ 0.15(s, 6 H,Si(CH3)2), 1.00 (s, 9 H, t-butyl), 3.85 (s, 3 H, CH3), 4.65 (s, 2 H, CH2O), 6.55 (dd, J =8.3, 1.0 Hz, 1 H) 6.66 (br s, 1 H), 7.80 (d, J =8.0 Hz, 1 H); MS (CI/NH3) m/e 296 (MH+) base, 186, 164.

EXAMPLE 11

Synthesis of 5,11-Dihydro-9-(dimethyl-t-butylsilyloxymethyl) -6H-pyrido [2,3-b][1,4 ]benzodiazepine-6-one (14)

Intermediate 13 (2.95 g, 10 mmol) was added to solution of 2-amino-3-chloropyridine (1.4 g, 11 mmol) and potassium tert-butoxide (1.7 g, 15 mmol) in 20 mL of dry THF. After 2 h the solvent was evaporated and the crude product was crystallized from petroleum ether to yield 1.4 g (36%) of N-(3 '-amino-2'-chloropyridyl ) -2 -amino-4-[(dimethyl-t-butylsilyloxy)methyl]benzamide as a white waxy solid: 1H NMR (CDCl3) δ 0.15 (s, 6 H, Si(CH3)2), 1.00 (s, 9 H, t-butyl), 4.80 (s, 2 H, CH2O), 5.80 (br s, 2 H, NH2), 6.75 (d, J =8.0 Hz, 1 H), 6.80 (s, 1 H), 7.35 (dd, J =8.2, 4.7 Hz, 1 H), 7.56 (d, J =8.2, 1 H), 8.20 (dd, J =4.7, 1.7 Hz, 1 H), 8.45 (br s, 1 H, NH), 8.80 (dd, J =8.2, 1.7 Hz, 1 H).

Irradiation at δ 7.56 collapsed the doublet at δ 6.75 to a singlet, irradiation at δ 8.20 collapsed each double doublet at δ 7.35 and δ 8.80 to a doublet (J =8.2 and 8.2 Hz), and irradiation at δ 8.80 collapsed each double doublet at δ 7.35 and δ 8.20 to a doublet (J =4.7 and 4.7 Hz); MS (CI/NH3) m/e 392 (MH+,base) , 334, 281, 264.

This intermediate (750 mg, 1.9 mmol) and p-toluene sulfonic acid (25 mg, 0.13 mmol) were suspended in 20 mL of toluene. The toluene was removed leaving a waxy solid which was heated at 215° C. for 15 min. Part of the resulting brown solid was purified on a silica gel column to give pure 14: 1H NMR (CDCl3) δ 0.15 (s, 6 H, Si(CH3)2], 1.00 (s, 9 H, t-butyl), 4.75 (s, 2 H, CH2O), 6.75 (s, 1 H), 6.92 (m, 2 H), 7.15 (d, J =7.7 Hz, 1 H) , 7.92 (m, 2 H) , Irradiation at δ 7.92 collapsed the signal at δ 6.92 to a doublet (J =7.7 Hz) and a singlet; MS (CI/NH3) m/e 356 (MH+, base), 315, 251.

EXAMPLE 12

Synthesis of 5,11-Dihydro-9-(dimethyl-t-butylsilyloxymethyl)-11- [(4-methyl-1-piperazinyl)acetyl]-6H-pyrido[2,3-b][1,4 ]benzodiazepine-6-one (15)

Compound 15 was made from crude compound 14 according to general procedure A. The crude product was crystallized from chloroform/hexane and further purified on a column to yield 68 mg (7.1% based on 13) of 15; mp 245°-248° C.: 1H NMR (CDCl3) δ 0.15 (s, 6 H, Si(CH3)2], 0.95 (s, 9 H, t-butyl), 1.50-2.50 (m, 8 H), 2.15 (s, 3 H, CH3), 3.20 (d, J =m14 Hz, 1 H), 3.50 (m, 1 H), 4.82 (s, 2 H, CH2O), 7.32 (dd, J =7.9, 3.2 Hz, 1 H) 7.41 (d, J =8.0 Hz, 1 H), 7.60 (dd, J =7.9, 1.3 Hz, 1 H), 7.94 (d, J =8.1 Hz, 1 H) , 8.20 (br s, 1 H) , 10.17 (br s, 1 H); MS (CI/NH3) m/e 496 (MH+, base), 463, 396, 356, 113.

EXAMPLE 13

Synthesis of 5,11-Dihydro-9-hydroxymethyl-11-[(4-methyl-1-piperazinyl)acetyl]-6H-pyrido [2,3 -b ][1,4 ]benzodiazepine-6-one (16)

Compound 15 (15 mg, 0.03 mmol) was dissolved in 1 mL CHCl3, and a solution of 1M tetrabutylammonium fluoride in THF (40 μl) was added. The solution was allowed to stand at room temperature overnight. The solvent was removed in vacuo, and the remaining residue was dissolved in saturated NaHCO3, washed with ether to remove non-polar impurities, and extracted with CHCl3. The CHCl3 extracts were combined, evaporated, and purified on a short silica gel column to yield 10 mg (86%) of 16 as a waxy solid: 1H NMR (CDCl3) δ 2.05-2.50 [m, 60H), 2.20 (s, 3 H, CH3), 3.22 (d, J =14 Hz, 1 H), 3.60 (m, 1 H), 4.80 (s, 2 H, CH2O), 7.30 (dd, J =7.8, 4.7 Hz, 1 H), 7.44 (d, J =8.1 Hz, 1 H), 7.50 (dd, J =1.6, 7.8 Hz, 1 H), 7.62 (s, 1 H), 7.96 (d, J =8.1 Hz, 1 H), 8.02 (m, 1 H); MS (CI/NH3) m/e 382 (MH+, base), 242, 141, 113.

EXAMPLE 14

Synthesis of 5-Ethyl-ll-hydro-[(4-methyl-1-piperazinyl)acetyl]-6H-pyrido[2,3-b][1,4]-benzodiazepine-6-one (17a)

5-Ethyl-ll-hydro-6H-pyrido[2,3-b][1,4]-benzodiazepine-6-one was prepared according to literature and condensed according to general procedure A to yield compound 17a. See Ogilvie, K. K.; Beaucage, S. L.; Schifman, A. L.; Theriault, N. Y.; Sadana, K. L.; *Can. J. Chem.*, 1978, 56, 2768, which is specifically incorporated by reference herein. 1H NMR (CDCl3) (HCl salt) 1.30–1.40(bs,3H), 2.05–2.40(m,3H), 2.75(s,3H,CH3), 2.90-3.60 (m, 8H) , 3.85 (m, 1H) , 4.40 (m, 1H) , 7.30–7.60 (m, 4H) , 7.78(d,J=7.7Hz,1H) , 7.81(d,J=7.5Hz,1H); MS(CI/NH3) m/e380 (MH+, base) , 240, 113, 101.

EXAMPLE 15

Synthesis of 5,11-Dihydro-11-[(1-piperazinyl) acetyl]-6H-pyrido[2,3-b][14]benzodiazepine-6-one (18)

Method A: Compound 18 was made from 6, 2-chloroacetyl chloride and excess piperazine using a modified procedure A.

Method B: Pirenzepine dihydrochloride (5.2 g, 11.3 mmol), a-chloroethyl chloroformate (10 mL), and N,N,N-diisopropylethylamine (20 mL) were suspended in 100 mL anhydrous CHCl3 and the mixture was refluxed for 1 h. The CHCl3 was removed in vacuo and the solid was dissolved in 50 mL of methanol and 5 mL of 1M HCl in ether (pH 1–2). The solution was refluxed for another 3 h before it was basified with aqueous sodium carbonate and washed with ether. The aqueous layer was saturated with NaCl and extracted into CHCl3 to yield 4.2 g (69%) of 18: 1H NMR (CDCl3) δ 2.00–2.80 (m, 8 H), 3.18 (br d, J =14.0 Hz, 1 H), 3.71 (d, J =14.0 Hz, 1 H), 7.30 (dd, J =4.7, 7.9 Hz, 1 H), 7.45 (m, 1 H), 7.63 (m, 3 H), 7.80 (m, 3 H), 7.97 (d, J =7.6 Hz, 1 H), 8.25 (br s, 1 H); MS (CI/NH3) m/e 338 (MH+, base), 212, 127.

GENERAL PROCEDURE D

Alkylation of 18

A solution of 18 (1 equiv), the appropriate halide (1.2 equiv), and triethylamine (2 equiv) in THF/MeOH (10/1) or DMF was stirred at 25°–40 ° C. until complete by TLC. All volatile materials were removed in vacuo, and the remaining residue was dissolved in 1 N HCl. The aqueous layer was washed with 3 equal portions of CH2C12, and then made basic ($\approx$pH 9) by addition of aqueous sodium carbonate. The product was extracted into CH2C12 (3×10 mL), and the combined organic layers were dried over Na2SO4, filtered, and evaporated in vacuo to give the crude product. The crude product was purified on a silica gel column (gradient mixture of 80 to 90% CHCl3, 10 to 20% MeOH, and 1 to 2% NH4OH) to give the corresponding N-alkyl derivatives (22–24).

General procedure for acylation of compound 18

Compound 18 (23.3 mg, 0.69 mmol) and methansulfonyl chloride (30 μL) were dissolved in 2 mL of chloroform. The solvent was evaporated and the residue was recrystallized from chloroform/ether to give the monohydrochloride of 5,11-dihydro-11-[(4-methanesulfonyl-1-piperazinyl)acetyl]-6H-pyrido[2,3-b][1,4]benzodiazepine-6-one (20) in 50% yield.

EXAMPLE 16

Synthesis of
5,11-Dihydro-11-[(4-propargyl-1-piperazinyl)acetyl]-6H-pyrido[2,3-b][1,4]benzodiazepine-6-one (22)

Compound 22 was made using general procedure D using intermediate 18 (42.3 mg, 0.125 mmol), propargyl bromide (22.4 mg, 0.188 retool), and triethylamine (35 μL, 0.251 mmol) in THF/MeOH. The product was recrystallized from CH2C12/MeOH to give 31.4 mg of pure 22 (67%): mp 249°–250° C; 1H NMR (CDCl3) δ 2.30–2.60 (br m, 8 H), 3.21–3.31 (m, 4 H), 3.46 (m, 1 H), 7.33 (m, 1 H), 7.44 (m, 1 H), 7.54–7.67 (m, 3 H), 7.93 (d, J =7.8 Hz, 1 H), 8.27 (br s, 1 H) ; MS (CI/NH3) m/e 376 (MH+, base) , 254, 212.

EXAMPLE 17

Synthesis of
5,11-Dihydro-11-[(4-benzyl-1-piperazinyl)acetyl]-6H-pyrido[2,3 -b ][1,4 ]benzodiazepine-6-one (23)

Compound 23 (41.1 mg, 98%) was made using general procedure D [18 (33.0 mg, 0.098 mmol), benzyl bromide (20.1 mg, 0.117 mmol), and triethylamine (27.3 μL, 0.196 mmol) in THF/MeOH]: 1H NMR (CDCl3) δ 1.93–2.51 (br m, 8 H) , 3.11 (d, J =14.4 Hz, 1 H), 3.32 (br s, 2 H), 3.54 (br d, J =14.4 Hz, 1 H), 7.16 (br m, 6 H), 7.36 (m, 1 H), 7.47 (d, J =6.9 Hz, 1 H), 7.56 (s, 1 H), 7.92 (d, J =7.8 Hz), 8.19 (br s, 1 H), 9.81 (br s, 1 H) ; MS (CI/NH3) m/e 428 (MH+, base), 254, 212, 177. The oxalate salt was prepared for pharmacological testing.

EXAMPLE 18

Synthesis of
5,11-Dihydro-11-[(4-[p-(N-[2-Boc-aminoethyl]carboxamido)benzyl]-1-piperazinyl)acetyl]-6H-pyrido[2,3-b][1,4]benzodiazepine-6-one (24b)

Compound 24b (197 mg, 72%) was made using general procedure D [18 (150 mg, 0.445 mmol), p-bromomethyl-N-(2-Boc-aminoethyl)benzamide (175 mg, 0.489 mmol) , and triethylamine (155 μL, 1.11 retool) in THF/MeOH]. See Shai, Y.; Kirk, K. L.; Channing, M. A.; Dunn, B. B.; Lesniak, M. A.; Eastman, R. C.; Finn, R. D.; Roth, J.; Jacobson, K. A.; *Biochemistry* 1989, 28, 4801, which is specifically incorporated by reference herein.

EXAMPLE 19

Synthesis of
5,11-Dihydro-ll-[(4-[2-hydroxyethyl]-1-piperazinyl)acetyl]-6H-pyrido[2,3-b][1,4]benzodiazepine-6-one (25)

Compound 18 (103 mg, 0.31 mmol) and 2-iodoethanol (0.6 g, 3.5 mmol) were dissolved in 4 mL of ethanol and heated at 95° C. for 3 h. The volatile material was removed in vacuo and the crude product was crystallized from ethyl acetate/isopropanol to give 77 mg of 25 (65%); mp 197°–200° C.; 1H NMR (CDCl3, free base) δ 2.00–2.70 (m, 10 H), 3.30 (d, 1 H), 3.50–3.70 (m, 4 H), 7.95 (d, 1 H), 8.30 (s, 1 H), 9.50 (br s, 1 H); MS (CI/NH3) m/e 382 (MH+base), 252, 212.

EXAMPLE 20

Synthesis of
5,11-Dihydro-ll-[(4-[2-chloroethyl]-1-piperazinyl)acetyl]-6H-pyrido[2,3-b][1,4]benzodiazepine-6-one dihydrochloride (26)

Compound 25 (110 mg, 0.22 mmol) was refluxed for 1 h with thionyl chloride (1 mL) in chloroform (4 mL). The volatile material was removed in vacuo, and the residue was basified with aqueous Na2CO3 (pH 10) and washed immediately with ether to completely remove the non polar impurity (TLC CHCl3/CH3OH/NH4OH: 9/1/0.1, Rf 0.4). The product was extracted into CHCl3 from the cold aqueous phase and the combined CHCl3 layers were concentrated in vacuo and acidified using ether/HCl. The precipitate was dried in vacuo to yield 29 mg of 26 (25%) as a white solid: mp 188–190° C.; 1H NMR (D20, HCl salt) δ 3.00–4.00 (m, 14 H), 7.50–7.70 (m, 3 H), 7.70–7.90 (m, 3 H), 8.40 (s, 1 H); MS (CI/NH3) m/e 400 (MH+), 212 (base), 364, 338. FAB mass spectroscopy showed peaks at mass 438 (M +K), 422 (M +Na), 400 (M +H), 364, 329, 307, 289, 211, 154, and 136. The salt was stable upon storage at −20 ° C. for at least 6 months.

EXAMPLE 21

Synthesis of
5,11-Dihydro-11-[(4-[2-aminoethyl]-1-piperazinyl)acetyl]-6H-pyrido[2,3-b][1,4]benzodiazepine-6-one (27)

Compound 26 (8.6 mg,0.017 mmol) was dissolved in concentrated NH4OH (0.4 mL) and stirred overnight. The crude product was extracted into CHCl3, and the organic layer was evaporated to dryness. The remaining residue was recrystallized from chloroform/petroleum ether to yield 7.2 mg of 27 (97%); mp 188–190 ° C.: 1H NMR (CDCl3) δ 2.00–2.70 (m, 12 H), 3.20 (d, J=14 Hz,1 H), 3.60 (br d,J=14 Hz, 1 H), 7.26 (dd, J =7.8, 4.7 Hz, 1H), 7.40 (m, 1 H), 7.55 (dd, J =7.9, 1.4 Hz, 1 H), 7.58–7.62 (br s, 1 H), 7.92 (d, J =7.7 Hz, 1 H), 8.26 (br s, 1 H), 9.35 (br s, 1 H); MS (CI/NH3) m/e 381 (MH+base) , 338, 252, 212.

EXAMPLE 22

Synthesis of 5,11-Dihydro-11-[4-[2-N-acetyl)ethyl]-1-piperazinyl)acetyl]-6H-pyrido[2,3-b][1,4]benzodiazepine-6-one (28)

Compound 28 was made from 27 using general procedure C: mp 93–95 ° C.; 1H NMR (CDCl3) δ 2.00 (s, 3 H, CH3), 2.05–2.50 (m, 10 H), 3.00 (m, 2 H), 3.20 (m, 1 H), 3.70 (d,J=14 Hz, 1 H), 6.00 (br s, 1 H, NH), 7.30 (dd, J =7.9, 4.7 Hz, 1 H), 7.40 (m, 1 H), 7.60 (m, 2 H), 7.95 (d, J =7.6 Hz, 1H), 8.25 (br s, 1H), 10.30 (br s, 1 H, NH); MS (CI/NH3) m/e 423 (MH+base) , 252, 212.

EXAMPLE 23

Synthesis of 5,11-Dihydro-11-[4-[2-(N-[3-Boc-amino-1-oxopropyl-]amino)ethyl]-1-piperazinyl)acetyl]-6H-pyrido[2,3-b][1,4]benzodiazepine-6-one (29a)

Compound 27 (100 mg, 0.28 mmol) was dissolved in 10 mL CHCl3, N-t-Boc-2-alanine-N-hydroxysuccinimide ester (70 mg, 0.27 mmol) was added in one portion and the reaction mixture was stirred at room temperature for 6 h. The mixture was basified (aqueous K2CO3) and extracted with CHCl3. The crude product was purified on silica gel column (gradient mixture of 80 to 90% CHCl3, 10 to 20% MeOH, and 1 to 2% NH4OH) to yield 135.9 mg of 29a (90%) as a white solid, mp 110–°115° C.(dec): 1H NMR (CDCl3) δ 1.40 (s, 9H, 3 CH3), 2.0–2.55 (m, 14H), 3.0 (m, 1H), 3.5 (s, 2H), 3.7 (m, 1H), 7.30 (dd, J =7.9, 4.7, 1H), 7.40 (m, 1H), 7.58–7.64 (m, 2H), 7.93 (d, J =7.7 Hz, 1H), 8.26 (bs, 1H), 9.80 (br s, 1 H); MS (CI/NH3) 552 (MH+), 478, 452, 301, 211.

EXAMPLE 24

5,11-Dihydro-11- [4- [2- (N-[4-Boc-amino-1-oxobutyl]amino) ethyl ]-1-piperaz inyl ) acetyl]-6H-pyrido [2,3-b][1,4]benzodiazepine-6-one (29b)

Compound 27 (100 mg, 0.28 mmol) was dissolved in 5 mL DMF. N-t-Boc-4-aminobutyric acid (58 mg, 0.28 mmol) were added followed by 1,3-dicyclohexylcarbodiimide (59 mg, 0.28 mmol) and 1-hydroxybenzotriazole (58 mg, 0.35 mmol). The mixture was stirred for 48 h at room temperature, diluted with water, extracted with CHCl3, dried and chromatographed on a silica gel column (CHCl3/MeOH/NH4OH 80/20/2) to yield 95 mg (64%) of 29b, mp 135° C. (dec). 1H NMR (CDCl3) δ 1.42 (s, 9 H, (CH3)3), 3.50–3.70(m,4H) , NH), 7.30 (dd, J =7.9, 4.7 Hz, 1 H), 7.40 (m, 1 H), 7.58–7.68 (m, 2 H), 7.95 (d, J =7.8 Hz, 1 H), 8.25 (br s, 1 H), 9.30 (br s, 1 H, NH); MS (EI) m/e 565 (MH+), 491, 350 (base), 253,211.

EXAMPLE 25

Synthesis of 5,11-Dihydro-11- [4- [2- (N-[6-Boc-aminohexyl]amino)ethyl]-1-piperazinyl)acetyl]-6H-pyrido[2,3-b][1,4]benzodiazepine-6-one (32d).

t-Butyloxycarbonylhexanoic acid was converted to the corresponding N,O-dimethylhydroxamate in 94% yield using DCC/dimethylaminopyridine in methylene chloride by the procedure of Martinez et al. See Martinez, J.; Bali, J. P.; Rodriguez, M.; Castro, B. et al, *J. Med. Chem.*, 1985, 28, 1874, which is specifically incorporated by reference herein.

The hydroxamate was then treated with lithium aluminum hydride at 0° C. in THF to give t-butyloxycarbonylhexanal in 90% yield. Compound 18 (35 mg, 0.1 mmol) and t-butyloxycarbonylhexanal (20 mg, 0.09 mmol) were dissolved in THF containing a minimum of MeOH and treated 4 Å molecular sieves and sodium cyanoborohydride (6.6 mg, 0.1 mmol).

After 24 h, the mixture was filtered and the solvent evaporated. The residue was taken up in ethyl acetate and extracted into 1M citric acid. The aqueous layer was washed with ethyl acetate and basified, and the crude product was recovered upon evaporation of the organic layer. The product was chromatographed on a silica gel column (CHCl3/MeOH/NH4OH 80/20/2) to yield 11 mg (20%) of 32d.

GENERAL PROCEDURE E

Alkylation of 18 with Bromoalkylphthalimides (33a–33h).

5-Bromohexylphthalimide (280 mg, 0.87 mmol), prepared by alkylation of potassium phthalimide with 1,5-dibromohexane in DMF, compound 18 (203 mg, 0.60 mmol) and triethylamine (0.21 mL) were combined in DMF and stirred for several days at room temperature. As the reaction proceeded with additional quantities of 5-bromohexylphthalimide and triethylamine were added.

The DMF was removed by azeotropic distillation with benzene and petroleum ether, leaving an orange oil, which crystallized overnight to yield 257 mg (75%) of 5,11-dihydro-11-[4-[2-(N-[6-phthaloylamino-1-oxohexyl]amino)ethyl]-1-piperazinyl)acetyl]-6H-pyrido[2,3-b][1,4]benzodiazepine-6-one (33d). The phthaloyl group was removed using hydrazine hydrate in EtOH/MeOH.

GENERAL PROCEDURE F

Alkylation/Amination of 18 with Dibromoalkanes and Ammonium Hydroxide (34a–34h).

Compound 18 (1 equivalent), a 1,n-dibromoalkane (n=3–10, 10 molar equivalents) and triethylamine (5 molar equivalents) were dissolved in methanol and stirred at room temperature (12–24 h). The mixture was then acidified (aqueous HCl) and washed with ether. The resulting aqueous phase was basified and extracted with CHCl3, and the chloroformic extracts were combined and evaporated.

The residue was dissolved in concentrated NH4OH/methanol and stirred at room temperature (40–72 h). The solvent was then removed, and the crude product was chromatographed on a silica gel column using 60–90% CHCl3 and 10–40% MeOH/NH4OH (10/1, v/v) as eluent.

EXAMPLE 26

Synthesis of 5,11-Dihydro-11-[(4-[10-aminodecyl]-1-piperazinyl)acetyl]-6H-pyrido[2,3-b][1,4]-benzodiazepine-6-one (34h); mp 95–97 ° C.; 1H NMR (CDCl3) δ 1.10–1.50 (m, 16 H), 2.10–2.70 (m, 12 H), 3.15 (d, J=14 Hz,1 H), 3.60 (br d, J=14 Hz,1 H), 7.30 (dd, J=7.9, 4.7 Hz, 1H), 7.40 (m, 1 H), 7.58 (dd, J=7.8, 1.4 Hz, 1 H), 7.70 (d, J=3.8 Hz, 1 H), 7.96 (d, J=7.7 Hz, 1 H), 8.28 (br s, 1 H); MS (CI/NH3) m/e 493 (MH+base), 254, 212. Detection of Aziridinium Intermediate.

For the 1H NMR studies of reaction kinetics, the hydrochloride salt of 26 (4 mg) was dissolved in 0.5 mL 100 mM K2DPO4-and2PO4 buffer (pD 7.4). The NMR tube was immediately inserted in the Varian 500 MHz proton NMR probe which had been heated to 37 ° C., and spectra were recorded at regular intervals. Relative amounts of the chloroethyl derivative 26 and its conversion products at various times were obtained by integration or by measuring relatives height (for the aziridinium salt) and assuming that 26 was converted quantitatively to 25 and the O-phosphate ester, via the aziridinium ion.

Rate constants for the cyclization of 26 and for the formation of 25 were obtained from the first order rate equations as described above. The concentration of the aziridinium ion as a function of time was fitted by non-linear regression analysis.

Binding Assay.

Inhibition of [3H]NMS binding in membranes from rat heart cells or in transfected rat A9L cells (from connective tissue) expressing m1, m3, or m4 muscarinic receptors (obtained from Dr. M. Brann, NIH) was measured.

A crude membrane fraction was obtained as follows. Confluent cultures were rinsed three times with phosphate-buffered saline, and lysed in a solution of 2 mM Tris-HCl (pH 7.1) and 1 mM EDTA for 30 min at 2° C. The cells were harvested by scraping and homogenized on a Polytron (10 sec, 75% mix).

Nuclei were removed in a low speed centrifugation (400 ×g, 5 min) and a crude membrane preparation was obtained by centrifugation of the supernatant at 50,000 x g for 20 min. The resulting pellet was resuspended in the lysis buffer and recentrifuged at 50,000 ×g for 20 min. Membranes were stored frozen at −70° C. until needed.

An aliquot of the membrane fraction (150–300 µg of protein) was incubated for 90 min at 37° C. with 0.5 nM [3H]-NMS and various concentrations of the unlabeled analogue in DMEM-Hepes. The total volume was 1 mL.

The incubation was terminated by rapid filtration over GF/B filters using a Brandel cell harvester. The filters were washed three times with ice-cold 0.9% NaCl, equilibrated in scintillation counting fluid and counted on a Beckmann LS 5801 liquid scintillation counter at 47% efficiency.

Non-specific binding was determined by co-incubation with 1 µM atropine, and amounted to less than 15% of total counts. It was routinely subtracted from the total counts.

To assay for irreversible inhibition, saturation by [3H]NMS before and after treatment of the membranes with the potential affinity label, was measured. Aliquots of brain membranes were incubated with 1.0 mM of freshly dissolved 26 in phosphate-buffered saline (pH 8.0) for 60 min at room temperature, then centrifuged at 15,000 rpm for 10 min.

The resulting pellet was resuspended in 25 mL of fresh phosphate-buffered saline (pH 7.2) and centrifuged as above. The pellet was again resuspended in fresh buffer, centrifuged, and aliquots were taken for [3H]NMS saturation binding experiments.

EXAMPLE 27

Synthesis of 4,9-Dihydro-3-methyl-4-[(1-piperazinyl)acetyl]-10H-thieno[3,4-b][1,5]benzodiazepin-10-one (38)

Telenzepine dihydrochloride (0.10 g, 0.23 mmol), α-chloroethyl chloroformate (0.2mL), and N,N,N-diisopropylethylamine (0.3 mL) were suspended in 100 mL anhydrous CHCl$_3$ and the mixture was refluxed for 2 h, treated with an additional 0.1 mL of diisopropylethylamine, and heated 10 min. The CHCl$_3$ was removed in vacuo and the solid (consisting mainly of the N-(α-chloroethyloxycarbonyl) intermediate which was not isolated) was dissolved in 7 mL of methanol and sufficient 1M HCl in ether to lower the pH to 0–1. The solution was refluxed for another 0.5 h and immediately basified with aqueous sodium carbonate and washed with ether. The aqueous layer was saturated with NaCl and extracted into CHCl$_3$ to yield 40 mg (50%) of 38. $^1$H NMR (CDCl$_3$) spectrum showed a characteristic singlet for the thiophene CH$_3$ at δ 2.43 ppm; MS (Cl/NH$_3$) m/e 353 (MH$^{30}$, base).

EXAMPLE 28

Synthesis of 4,9-Dihydro-3-methyl-4-[[4-(10-bromodecyl)-1-piperazinyl]-acetyl]-10H-thieno[3,4-b][1,5]benzodiazepin-10-one (39, n = 10).

A solution of 38 (20 mg, 57 µmol), 1,10-dibromodecane (0.22g. 0.73 mmol), and triethylamine (0.2mL) was stirred in MeOH (0.5 mL) at 25° C. for 3 days. The reaction was judged complete by TLC (Rf of product on silica, with chloroform:methanol:ammonia, 90:10:1, by volume was 0.66), and all volatile materials were removed in vacuo. The remaining residue was dissolved in 0.5N HCl. The acidic aqueous layer was washed with ether (2X), and then made basic (≈pH 9) by addition of 10% sodium carbonate. The product was extracted into CHCl$_3$ (3×), and the combined organic layers were dried over Na$_2$SO$_4$, filtered and evaporated in vacuo to give the crude product as a glass. Yield 20 mg (61%).

EXAMPLE 29

Synthesis of 4,9-Dihydro-3-methyl-4-[[4-(10-aminodecyl)-1-piperazinyl]-acetyl]-10H-thieno[3,4-b][1,5]benzodiazepin-10-one (40, n = 10).

Compound 39 (2.0 mg) was dissolved in 10 mL methanol and treated with 10 mL of concentrated NH$_4$OH. The solution was stirred for 2 days at room temperature and then for 12 h at 50° C. After evaporation, the crude product was purified on a silica gel TLC plate (developed with chloroform:methanol:ammonia, 90:10:1, by volume) to give pure product, Rf=0.35. FAB-MS spectrum showed a parent ion peak at 512 m/z (m+1).

The affinity of 40, n=10 for m1 receptors (K$_i$) was determined in radioligand binding assays to be 2.39 nM.

EXAMPLE 30

Synthesis of 5,11-Dihydro-11-[[4-[10-[(3-isothiocyanatophenyl)aminothiocarbonylamino]decyl]-1-piperazinyl]acetyl]-6H-pyrido[2,3-b][1,4]-benzodiazepine-6-one (41a, n=10).

5,11-Dihydro-11-[(4-[10-aminodecyl]-1-piperazinyl)acetyl]-6H-pyrido[2,3-b][1,4]-benzodiazepine-6-one (2.8 mg, 5.7 µmol) was dissolved in 0.2 mL DMF and treated with 1,3-phenylenediisothiocyanate (6 mg, 31 µmol). After 0.5 h, ethyl acetate (1 mL) and petroleum ether (3 mL) were added, and the cloudy mixture was stored at 4° C. overnight. The supernatant was decanted from the oily residue. The residue solidified upon trituration with dry ether to give 2.0 mg (51% yield) of pure product (R$_f$=0.35, silica, chloroform:methanol:acetic acid, 85:10:5, by volume). FAB-MS spectrum showed a parent ion peak at 685 m/z (m+1).

When incubated with membranes from rat forebrain tissue unrecoverable reduction in the Bma$_x$ at m1 receptors of 90–95% followed by thorough washing, compound 41a caused an unrecoverable reduction in the $B_{max}$ at m1 receptors of 90-95% (from saturation of treated vs. control membranes with [3H]NMS). Thus, this isothiocyanate derivative is a potent chemical affinity label for m1 receptors.

Preparation of Fluorescent probes

Compounds 34 and 40 were coupled to activate fluorescent dye moieties, such as fluorescein isothiocyanate, tetramethylrhodamine isothiocyanate, NBD, Texas red, etc. to form fluorescent conjugates that retained high affinity (in the range of $10^{-9}-10^{-7}$ M $K_i$ values). These probes can be applied to receptor assays for detection, assay or characterization, using methods outlined in McCabe et al, FASEB J., vol. 4, pp. 2934-2940 (1990) which is specifically incorporated by reference herein.

What is claimed is:

1. A compound having the formula:

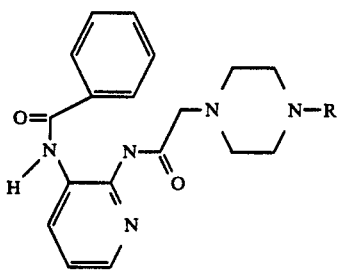

wherein R is selected from the group consisting of a substituted benzyl group other than a methyl benzyl, chlorobenzyl or methyloxide group, a chloroethyl group, an aminoethyl group, an ω-amino alkyl group, or an N-substituted ω-amino alkyl group.

2. A compound according to claim 1, wherein, R is selected from the group consisting of —CH$_2$C$_6$H$_4$-p-CONHCH$_3$, —CH$_2$C$_6$H$_4$-p-CONH(CH$_2$)$_2$NHBoc, —CH$_2$C$_6$H$_4$-p-CONH(CH$_2$)$_2$NH$_2$, —CHC$_6$H$_4$-p-CONH(CH$_2$)$_4$NHBoc, —(CH$_2$)$_2$Cl, —(CH$_2$)$_2$NH$_2$, —(CH$_2$)$_2$NHAc, —(CH$_2$)$_2$NHCO(CH$_2$)$_2$NHBoc, —(CH$_2$)$_2$NHCO(CH$_2$)$_3$NHBoc, —(CH$_2$)$_2$NHCO(CH$_2$)$_2$NH$_2$, —(CH$_2$)$_2$NHCO(CH$_2$)$_3$NH$_2$, —(CH$_2$)$_2$NHCO(CH$_2$)$_2$NHAc, —(CH$_2$)$_2$NHCO(CH$_2$)$_3$NHAC, —(CH$_2$)$_6$NHBoc, —(CH$_2$)$_3$NPth, —(CH$_2$)$_4$NPth, —(CH$_2$)$_5$NPth, —(CH$_2$)$_6$NPth, —(CH$_2$)$_3$NH$_2$, —(CH$_2$)$_4$NH$_2$, —(CH$_2$)$_5$NH$_2$, —(CH$_2$)$_6$NH$_2$, —(CH$_2$)$_7$NH$_2$, —(CH$_2$)$_8$NH$_2$, —(CH$_2$)$_9$NH$_2$, —(CH$_2$)$_{10}$NH$_2$, —(CH$_2$)$_9$NHAc, —(CH$_2$)$_{10}$NHAc, —(CH$_2$)$_{10}$NEt$_2$, —(CH$_2$)$_{10}$NHCH$_2$—(o-MeO)Ph, —(CH$_2$)$_n$—NHCSNH-aryl, —(CH$_2$)$_n$—NHCSNH—(C$_6$H$_4$)m—NCS, —(CH$_2$)$_n$—NHCSNH—(C$_6$H$_4$)p-NCS, —(CH$_2$)$_n$—NHCO-alkyl, —(CH$_2$)$_n$—NHCO-aryl, —(CH$_2$)$_n$—NH-X-biotin, —(CH$_2$)$_n$—NH-radiolabelling prosthetic group, and —(CH$_2$)$_n$—NH-Y;

wherein n is from 2 to 10, X is a spacer, alkyl is $C_nH_{2n+1}$, aryl is a $C_6-C_{14}$ ring structure, and Y is selected from the group consisting of a polymer, an antibody, a latex microparticle, and a magnetic particle.

3. A compound according to claim 1 wherein said compound has the ability to bind as an antagonist to a muscarinic receptor.

4. A compound according to claim 2, wherein R is —(CH$_2$)$_{10}$NH$_2$, which is conjugated to a fluorescent dye moiety.

5. A compound according to claim 4, wherein said fluorescent dye moiety is selected from the group consisting of flluorescein isothiocyanate, tetramethylrhodamine isothiocyanate, NBD, and Texas red.

6. A compound having the formula

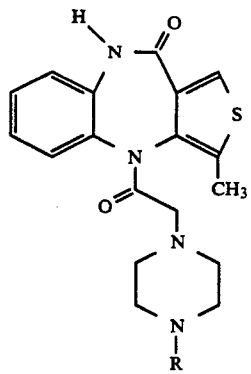

wherein R is selected from the group consisting of a propargyl group, a substituted benzyl group, a hydroxyethyl group, a chloroethyl group, an aminoethyl group, an ω-amino alkyl group, or an N-substituted ω-amino alkyl group.

wherein R is selected from the group consisting of a propargyl group, a substituted benzyl group, a hydroxyethyl group, a cloroethyl group, an aminoethyl group, an ω-amino alkyl group, or an N-substituted ω-amino alkyl group.

7. A compound according to claim 6, wherein, R is —CH$_2$C≡CH, —CH$_2$C$_6$H$_4$-p-CONHCH$_3$, —CH$_2$C$_6$H$_4$-p-CONH(CH$_2$)$_2$NHBoc, —CH$_2$C$_6$H$_4$-p-CONH(CH$_2$)$_2$NH$_2$, —CH$_2$C$_6$H$_4$-p-CONH(CH$_2$)$_4$NHBoc, —(CH$_2$)$_2$OH, —(CH$_2$)$_2$Cl, —(CH$_2$)$_2$NH$_2$, —(CH$_2$)$_2$NHAc, —(CH$_2$)$_2$NHCO(CH$_2$)$_2$NHBoc, —(CH$_2$)$_2$NHCO(CH$_2$)$_3$NHBoc, —(CH$_2$)$_5$NPth, —(CH$_2$)$_6$NPth, —(CH$_2$)$_3$NH$_2$, —(CH$_2$)$_4$NH$_2$, —(CH$_2$)$_5$NH$_2$, —(CH$_2$)$_6$NH$_2$, —(CH$_2$)$_7$NH$_2$, —(CH$_2$)$_8$NH$_2$, —(CH$_2$)$_9$NH$_2$, —(CH$_2$)$_{10}$NH$_2$, —(CH$_2$)$_9$NHAc, —(CH$_2$)$_{10}$NHAc, —(CH$_2$)$_{10}$NEt$_2$, —(CH$_2$)$_{10}$NHCH$_2$—(o-MeO)Ph, —(CH$_2$)$_n$—NHCSNH-aryl, —(CH$_2$)$_n$—NHCSNH—(C$_6$H$_4$)m—NCS, —(CH$_2$)$_n$NHCSNH—(C$_6$H$_4$)p—NCS, —(CH$_2$)$_n$—NHCO—alkyl, —(CH$_2$)$_n$—NHCO—aryl, —(CH$_2$)$_n$—NH-X-biotin, —(CH$_2$)$_n$—NH-radiolabelling prosthetic group, and —(CH$_2$)$_n$—NH—Y;

wherein n is from 2 to 10, X is a spacer, alkyl is $C_nH_{2n+1}$, aryl is a $C_6-C_{14}$ ring structure, and Y is selected from the group consisting of a polymer, an antibody a latex microparticle, and a magnetic particle.

8. A compound according to claim 6 wherein said compound has the ability to bind as an antagonist to a muscarinic receptor.

9. A compound according to claim 7, wherein R is —(CH$_2$)$_{10}$NH$_2$, which is conjugated to a fluorescent dye moiety.

10. A compound according to claim 9 wherein said fluorescent dye moiety is selected from the group consisting of fluorescein isothiocyanate, tetramethylrhodamine isothiocyanate, NBD, and Texas red.

* * * * *